(12) United States Patent
Boons et al.

(10) Patent No.: US 8,796,229 B2
(45) Date of Patent: Aug. 5, 2014

(54) FEEDBACK PRODRUG

(75) Inventors: Geert-Jan Boons, Athens, GA (US); Jun Guo, Athens, GA (US)

(73) Assignee: University of Georgia Research Foundation, Inc., Athens, GA (US)

(*) Notice: Subject to any disclaimer, the term of this patent is extended or adjusted under 35 U.S.C. 154(b) by 110 days.

(21) Appl. No.: 13/222,495

(22) Filed: Aug. 31, 2011

(65) Prior Publication Data
US 2012/0058960 A1    Mar. 8, 2012

Related U.S. Application Data

(63) Continuation of application No. 12/224,019, filed as application No. PCT/US2007/004100 on Feb. 16, 2007, now abandoned.

(60) Provisional application No. 60/774,009, filed on Feb. 16, 2006.

(51) Int. Cl.
  *A61K 47/00*    (2006.01)
  *A61K 47/48*    (2006.01)

(52) U.S. Cl.
  CPC ............... *A61K 47/48138* (2013.01)
  USPC ........... 514/25; 536/16.8; 536/17.6; 536/17.9

(58) Field of Classification Search
  CPC ................................ A61K 47/48138
  USPC .......................... 514/25; 536/16.8, 17.6, 17.9
  See application file for complete search history.

(56) References Cited

U.S. PATENT DOCUMENTS

| 4,966,848 | A  | 10/1990 | Smith et al. |
| 5,223,421 | A  | 6/1993  | Smith et al. |
| 5,837,218 | A  | 11/1998 | Peers et al. |
| 2003/0181359 | A1 | 9/2003 | Bebbington et al. |
| 2007/0275903 | A1 | 11/2007 | Bebbington et al. |

FOREIGN PATENT DOCUMENTS

WO   WO 2007/098033 A2   8/2007
WO   WO 2007/098033 A3   5/2008

OTHER PUBLICATIONS

Definition of derivative from http://cancerweb.ncl.ac.uk/omd/about.html, pp. 1-5. Accessed Jul. 7, 2005.*
Allen et al., "The Cambridge Crystallographic Data Centre: computer-based search, retrieval, analysis and display of information," Oct. 1979 *Acta Crystallogr.* B35(10): 2331-2339.
Allen et al., "Systematic analysis of structural data as a research technique in organic chemistry," May 1983 *Acc. Chem. Res.* 16(5):146-153.
"Arg9," product website [online]. AnaSpec, San Jose, CA, Copyright 2002-2006. [Retrieved on Nov. 25, 2008]. Retrieved from the Internet: <http://www.anaspec.com/products/product.asp?id=32166>; 1 page.
Asano et al., "Sugar-mimic glycosidase inhibitors: natural occurrence, biological activity and prospects for therapeutic application," May 5, 2000 *Tetrahedron: Asymmetry* 11(8):1645-1680.
Asano, "Glycosidase inhibitors: update and perspectives on practical use," Oct. 2003 *Glycobiology* 13(10):93R-104R. Available online on Jul. 8, 2003.
Berecibar et al., "Synthesis and biological activity of natural aminocyclopentitol glycosidase inhibitors: mannostatins, trehazolin, allosamidins, and their analogues," Mar. 10, 1999 *Chem. Rev.* 99(3):779-844. Available online on Feb. 19, 1999.
Bertozzi and Kiessling, "Chemical glycobiology," Mar. 23, 2001 *Science* 291(5512):2357-2364.
Böhm, "The computer program LUDI: A new method for the de novo design of enzyme inhibitors," Feb. 1992 *J Comp. Aided Mol. Design* 6(1):61-78.
Böhm, "LUDI: rule-based automatic design of new substituents for enzyme inhibitor leads," Dec. 1992 *J. Comp. Aided Mol. Design* 6(6):593-606.
Boons, "Novel approached for the design and synthesis of selective glycosidase inhibitors," Meeting Abstract presented at the Hudson Award Symposium [online]. Abstract No. CARB 14, Division of Carbohydrate Chemistry. *229th American Chemical Society (ACS) National Meeting.* San Diego, CA; Mar. 13-17, 2005. Available online [Retrieved on Sep. 18, 2008]. Retrieved from the Internet: <http://oasys2.confex.com/acs/229nm/techprogram/>; 1 page.
Boons, "Novel approached for the design and synthesis of selective glycosidase inhibitors," Slides presented at the Hudson Award Symposium [online]. Abstract No. CARB 14, Division of Carbohydrate Chemistry. *229th American Chemical Society (ACS) National Meeting.* San Diego, CA; Mar. 13-17, 2005. 21 pages.
Boss et al., "Synthesis and evaluation of aminocyclopentitol inhibitors of β-glucosidases," Jan. 27, 2000 *Org. Lett.* 2(2):151-154. Available online on Dec. 23, 1999.
"Cell permeable / drug delivery peptides," datasheet [online]. AnaSpec, San Jose, CA. No date available [Retrieved on Nov. 25, 2008]. Retrieved from the Internet: <http://www.anaspec.com/content/pdfs/c_literature102.pdf>; 3 pages.
de Groot et al., "Elongated multiple electronic cascade and cyclization spacer systems in activatible anticancer prodrugs for enhanced drug release," Dec. 28, 2001 *J. Org. Chem.* 66(26):8815-8830. Available online on Nov. 27, 2001.
de Melo et al., "α- and β-Glucosidase inhibitors: chemical structure and biological activity," Oct. 29, 2006 *Tetrahedron* 62(44):10277-10302. Available online on Sep. 7, 2006.
Dennis et al., "Growth inhibition of human melanoma tumor xenografts in athymic nude mice by swainsonine," Mar. 15, 1990 *Cancer Res.* 50(6):1867-1872.
Dennis et al., "Carbonoyloxy analogs of the anti-metastatic drug swainsonine. Activation in tumor cells by esterases," Oct. 19, 1993 *Biochem. Pharmacol.* 46(8):1459-1466.
Dennis et al., "Protein glycosylation in development and disease," May 1999 *Bioessays* 21(5):412-421.
Dennis et al., "Glycoprotein glycosylation and cancer progression," Dec. 6, 1999 *Biochim. Biophys. Acta* 1473(1):21-34.
Dube et al., "Glycans in cancer and inflammation—potential for therapeutics and diagnostics," Jun. 2005 *Nature Reviews Drug Discovery* 4(6):477-488.

(Continued)

*Primary Examiner* — Julie Ha
(74) *Attorney, Agent, or Firm* — Mueting, Raasch & Gebhardt, P.A.

(57) ABSTRACT

Compounds and methods for use in selectively inhibiting a lytic enzyme based on feedback inhibition are described. The conjugated compound serves as a substrate for a lytic enzyme. Cleavage of the conjugated compound by the lytic enzyme releases an inhibitor of the enzyme.

8 Claims, 11 Drawing Sheets

(56) References Cited

OTHER PUBLICATIONS

Dwek, "Glycobiology: toward understanding the function of sugars," Mar. 28, 1996 *Chem. Rev.* 96(2):683-720.

Ekhart et al., "Tables of glycosidase inhibitors," in *Iminosugars as Glycosidase Inhibitors: Nojirimycin and Beyond*; Stütz (Ed.); Wiley-VCH: New York, NY; 1999. Title page, publishers page and pp. 254-390.

Elbein, "Glycosidase inhibitors: inhibitors of N-linked oligosaccharide processing," Dec. 1991 *FASEB J.* 5(15):3055-3063.

Fischer et al., "A stepwise dissection of the intracellular fate of cationic cell-penetrating peptides," Mar. 26, 2004 *J. Biol. Chem.* 279(13):12625-12635. Available online on Jan. 5, 2004.

Fuster and Esko, "The sweet and sour of cancer: glycans as novel therapeutic targets," Jul. 2005 *Nature Reviews Cancer* 5(7):526-542.

Goss et al., "Inhibitors of carbohydrate processing: A new class of anticancer agents," Sep. 1995 *Clin. Cancer Res.* 1(9):935-944.

Guo et al., "Feedback inhibition prodrug for selectively targeting mannosides," Meeting abstract. *231st ACS National Meeting of the American Chemical Society*. Atlanta, GA. Mar. 26-30, 2006.

Guo et al., "Selective inhibition of glycosidases by feedback prodrugs," 2006 *Angew. Chem. Int. Ed.* 45:5345-5348. Available online on Jul. 17, 2006.

Hambley et al., "Crystal and molecular structure of methotrexate," Apr. 16, 1986 *J Am. Chem. Soc.* 108(8):2103-2105.

Heightman and Vasella, "Recent insights into inhibition, structure, and mechanism of configuration-retaining glycosidases," Mar. 15, 1999 *Angew. Chem. Int. Ed.* 38(6):750-770.

"Insight II®" product manual [online]. Molecular Simulation, Inc.; San Diego, CA. Jun. 2000 [Retrieved on Sep. 18, 2008]. Retrieved from the Internet: <http://cesario.rutgers.edu/software-manuals/insightIImanual.pdf>; Title page publishers page and table of contents only; 28 pages.

Kawatkar et al., "Structural basis of the inhibition of golgi α-mannosidase ii by mannostatin a and the role of the thiomethyl moiety in ligand-protein interactions," Jun. 28, 2006 *J. Am. Chem. Soc.* 128(25):8310-8319. Available online on Jun. 2, 2006.

King and Ganem, "Synthetic studies on mannostatin a and its derivatives: a new family of glycoprotein processing inhibitors," Jan. 26, 1994 *J. Am Chem. Soc.* 116(2):562-570.

Kleban et al., "Amino(hydroxymethyl)cyclopentanetriols, an emerging class of potent glycosidase inhibitors—Part I: Synthesis and evaluation of β-$_D$-pyranoside analogues in the *manno, gluco, galacto*, and GlcNAc series," May 4, 2001 *ChemBioChem.* 2(5):365-368.

Kolter and Sandhoff, "Sphingolipids—their metabolic pathways and the pathobiochemistry of neurodegenerative diseases," Jun. 1, 1999 *Angew. Chem. Int. Ed.* 38(11):1532-1568. Available online on May 26, 1999.

Li et al., "Inhibition of golgi mannosidase II with mannostatin A analogues: synthesis, biological evaluation, and structure-activity relationship studies," Sep. 6, 2004 *ChemBioChem* 5:1220-1227.

Lillelund et al., "Recent developments of transition-state analogue glycosidase inhibitors of non-natural product origin," Feb. 2002 *Chem. Rev.* 102:515-553. Available online on Jan. 29, 2002.

"Ludi," datasheet [online]. Accelrys, Inc.; San Diego, CA. [Retrieved on Sep. 18, 2008]. Released Mar. 2005. Retrieved from the Internet: <http://caligari.dartmouth.edu/doc/insightII/ludi/2-TheoTOC.doc.html>; 3 pages.

*McGraw-Hill Dictionary of Scientific and Technical Terms, Fourth Edition*, 1989, McGraw-Hill Book Co., New York. Title Page, Copyright Page, Table of Contents, and p. 1218. (4 pages).

"Moiety," as defined on Dictionary.com. Available online [Retrieved on Aug. 26, 2010]. Retrieved from the Internet: <http://dictionary.reference.com/browse/moiety>; 3 pages.

Moremen, Kelly "Selective Mannosidase Inhibitors as Cancer Therapeutics," Grant Abstract, Grant No. 1U01CA091295-01 [online]. National Cancer Institute, National Institutes of Health, project dates Jun. 6, 2001 to May 31, 2005 [Retrieved on Sep. 17, 2008]. Retrieved from the Internet: <http://crisp.cit.nih.gov/crisp/CRISP_LIB.getdoc?textkey=6334113&p_grant_num=1U01CA091295-01&p_query=&ticket=76193539&p_audit_session_id=363398315&p_keywords=>; 2 pages.

Moremen, Kelly "Selective Mannosidase Inhibitors as Cancer Therapeutics," Grant Abstract, Grant No. 5U01CA091295-02 [online]. National Cancer Institute, National Institutes of Health, project dates Jun. 6, 2001 to May 31, 2005 [Retrieved on Sep. 17, 2008]. Retrieved from the Internet: <http://crisp.cit.nih.gov/crisp/CRISP_LIB.getdoc?textkey=6515081&p_grant_num=5U01CA091295-02&p_query=&ticket=76193539&p_audit_session_id=363398315&p_keywords=>; 2 pages.

Moremen, Kelly "Selective Mannosidase Inhibitors as Cancer Therapeutics," Grant Abstract, Grant No. 5U01CA091295-03 [online]. National Cancer Institute, National Institutes of Health, project dates Jun. 6, 2001 to May 31, 2005 [Retrieved on Sep. 17, 2008]. Retrieved from the Internet: <http://crisp.cit.nih.gov/crisp/CRISP_LIB.getdoc?textkey=6613861&p_grant_num=5U01CA091295-03&p_query=&ticket=76193539&p_audit_session_id=363398315&p_keywords=>; 2 pages.

Moremen, Kelly "Selective Mannosidase Inhibitors as Cancer Therapeutics," Grant Abstract, Grant No. 5U01CA091295-04 [online]. National Cancer Institute, National Institutes of Health, project dates Jun. 6, 2001 to May 31, 2006 [Retrieved on Sep. 17, 2008]. Retrieved from the Internet: <http://crisp.cit.nih.gov/crisp/CRISP_LIB.getdoc?textkey=6740790&p_grant_num=5U01CA091295-04&p_query=&ticket=76193539&p_audit_session_id=363398315&p_keywords=>; 2 pages.

Ogawa and Washida, "Synthesis and glycosidase inhibitory activity of five stereoisomers of 5-amino-5-c-methyl-1,2,3,4-cyclopentanetetrol," Sep. 1998 *Eur. J. Org. Chem.* 1998(9):1929-1934.

Ogawa et al., "Synthesis and biological evaluation of α-mannosidase inhibitory activity of three deoxy derivatives of mannostatin A," Jun. 7, 1999 *Bioorg. Med. Chem. Lett.* 9(11):1499-1504.

Ogawa et al., "Synthesis of a potent aminocyclitol α-mannosidase inhibitor, 1L-(1,2,3,5/4)-5-amino-4-O-methyl-1,2,3,4-cyclopentanetetrol," May 2000 *Bioorg. Med. Chem. Lett.* 10(10):1047-1050.

Pardee and Reddy, "Beginnings of feedback inhibition, allostery, and multi-protein complexes," Dec. 4, 2003 *Gene* 321:17-23.

Popowycz et al., "Derivatives of (2R,3R,4S)-2-aminomethylpyrrolidine-3,4-diol are selective α-mannosidase inhibitors," Sep. 17, 2001 *Bioorg Med. Chem. Lett* 11(18):2489-2493.

Sarkar et al., "Disaccharide uptake and priming in animal cells: inhibition of sialyl Lewis X by acetylated Galβ1→4GlcNAcβ-O-naphthalenemethanol," Apr. 11, 1995 *Proc. Natl. Acad. Sci. USA* 92(8):3323-3327.

Tropea et al., "Mannostatin A, a new glycoprotein-processing inhibitor," Oct. 30, 1990 *Biochemistry* 29(43):10062-10069.

Varki, "Biological roles of oligosaccharides: all of the theories are correct," Apr. 1993 *Glycobiology* 3(2):97-130.

von Itzstein and Johnson, "Sialic acids and sialic acid-recognising proteins: drug discovery targets and potential glycopharmaceuticals," 1997 *Curr. Med. Chem.* 4(3):185-210.

Wilson et al., "Investigation of the stability of thiosialosides toward hydrolysis by sialidases using NMR spectroscopy," Aug. 12, 1999 *Org. Lett.* 1(3):443-446. Available online on Jul. 3, 1999.

Yuasa et al., "Design Syntheses of Inhibitors of Glycoenzymes," Jul. 2002 *Trends Glycosci. Glycotechnol.* 14(78):231-251.

International Preliminary Report on Patentability for International Application No. PCT/US2007/004100, issued Aug. 19, 2008; 8 pgs.

International Search Report for International Application No. PCT/US2007/004100, mailed Mar. 19, 2008; 4 pgs.

Office Action dated Jul. 23, 2010, for U.S. Appl. No. 12/224,019; 9 pgs.

Office Action dated Nov. 1, 2010, for U.S. Appl. No. 12/224,019; 20 pgs.

Office Action dated May 5, 2011, for U.S. Appl. No. 12/224,019; 28 pgs.

Written Opinion issued by the International Searching Authority for International Application No. PCT/US2007/004100, mailed Mar. 19, 2008; 7 pgs.

\* cited by examiner

Scheme 1

Scheme 2.

Linker design using LUDI:

Hits from LUDI run

Compounds were docked using Autodock

| R | ΔG$_{binding}$ (Kcal/mol) | K$_i$ (nM) |
|---|---|---|
| (ethyl-pyrrole-NH₂) | -10.2 | 34.8 |
| (ethyl-phenyl-NH₂) | -10.3 | 28.4 |
| (methoxy-indole-ethyl) | -9.9 | 59.2 |
| (methyl-bromo-aniline) | -10.4 | 24.5 |
| (methyl-bromo-aniline) | -10.1 | 36.0 |

Fig. 10

Inhibition of Human Golgi and Lysosomal Mannosidase

| R | | HGMII $K_i$ (μmol) | HLM $K_i$ (μmol) | HGMII $K_i$ (μmol) | HLM $K_i$ (μmol) |
|---|---|---|---|---|---|
| a: | H | 0.21 | 0.09 | 50 | 6.6 |
| b: | F-C6H4-CH2 | 0.88 | 0.11 | 10 | 0.45 |
| c: | Cl-C6H4-CH2 | 0.53 | 0.17 | 6.0 | 0.33 |
| d: | Br-C6H4-CH2 | 0.91 | 0.10 | 8.1 | 0.67 |
| e: | (phenyl)-CH2 | 0.51 | 0.05 | 7.6 | 0.33 |
| f: | MeO-C6H4-CH2 | 0.52 | 0.10 | 6.6 | 0.48 |
| g: | AllO-C(O)-C6H4-CH2 | 3.22 | 0.14 | 4.4 | 0.16 |

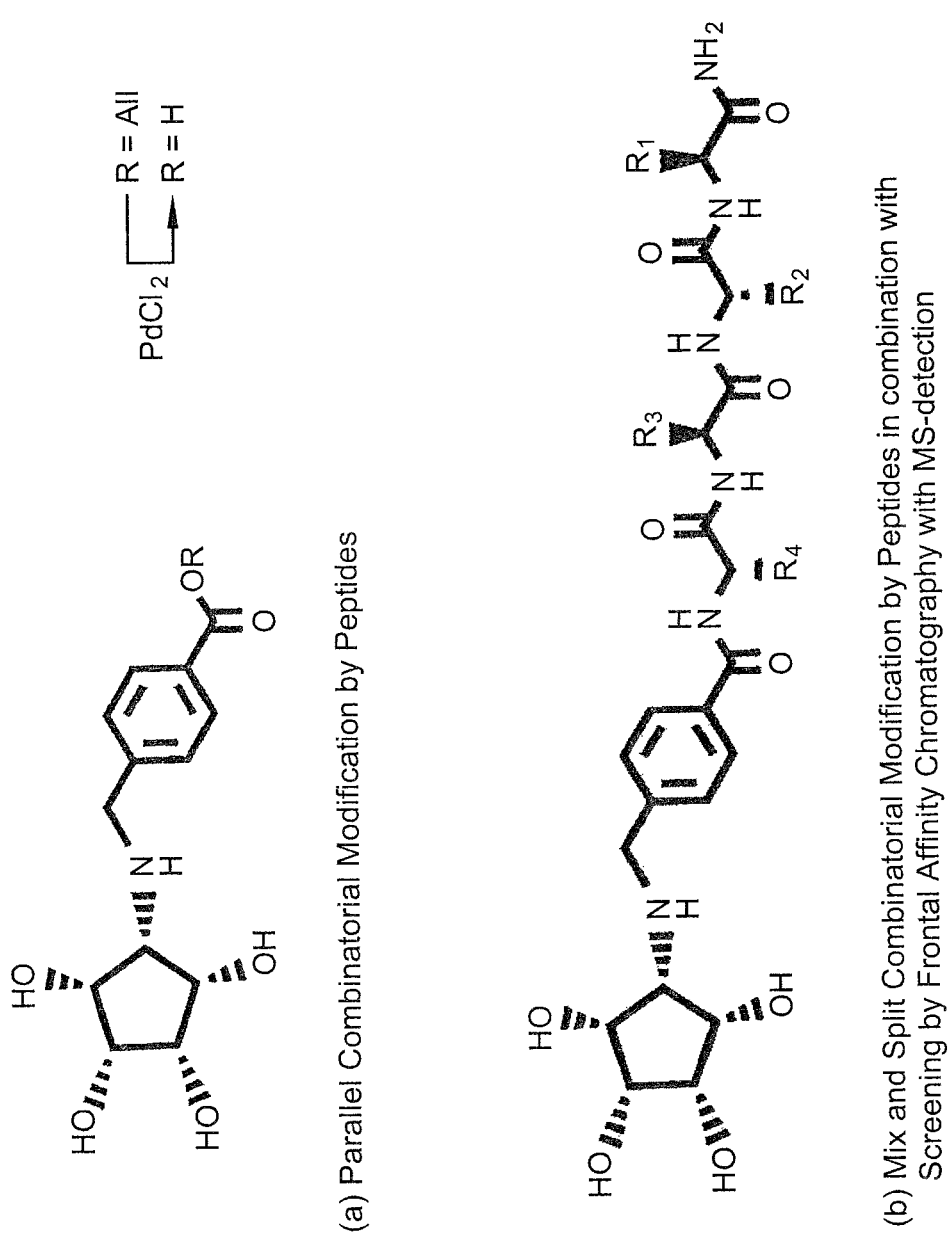

FEEDBACK PRODRUG

This application is a continuation patent application of U.S. patent application Ser. No. 12/224,019, filed on Aug. 14, 2008 now abandoned, which is a National Stage entry of PCT/US2007/004100, filed on Feb. 16, 2007, which claims the benefit of U.S. Provisional Application Ser. No. 60/774,009, filed Feb. 16, 2006, each of which is incorporated herein by reference in its entirety.

STATEMENT OF GOVERNMENT RIGHTS

This invention was made with government support under a grant from the National Cancer Institute, National Institutes of Health, Grant No. 5U01CA91295. The U.S. Government has certain rights in this invention.

BACKGROUND

Protein- and lipid-linked oligosaccharides at the surface of eukaryotic cells are responsible for a wide range of biological processes impacting health and disease. Examples of such processes include fertilization, embryogenesis, neuronal development, hormone activities, the proliferation of cells and their organization into specific tissues. Remarkable changes in cell-surface carbohydrates occur with tumor progression, which appears to be intimately associated with the dreaded state of metastasis. Furthermore, carbohydrates of host cells are often employed by pathogens for cell entry. Not surprisingly, compounds that can interfere in the biosynthesis of oligosaccharides are regarded as attractive leads for drug discovery for wide range of diseases. They also have great potential as agrochemicals, for example as insecticides and fungicides.

Much effort has expended on the development of glycosidase inhibitors, many of which have been isolated from plants and microorganisms. These compounds are often alkaloids whose structures resemble that of monosaccharides. A serious drawback of the use of these alkaloids as drugs is that they inhibit a wide range of glycosidases. Although many analogs of natural glycosidase inhibitors have been synthesized, these efforts have rarely resulted in a selective inhibitor. As a result, only a very small number of glycosidase inhibitors have been successfully developed as therapeutics.

SUMMARY OF THE INVENTION

The invention provides compounds and methods for use in selective inhibition of a lytic enzyme based on feedback inhibition. An inhibitor of the enzyme is released by enzyme-mediated hydrolysis of a conjugated compound, which subsequently inhibits the enzyme that initiated the release of the inhibitor. The conjugated compounds of the invention are frequently referred herein as "prodrugs". An enzyme inhibitor that is released by the action of the enzyme it inhibits displays an improved selectivity because of the exquisite selectivity of enzymes for their substrates. Optional O-acetylation of the prodrug facilitates cellular uptake. Hydrolysis of the acetyl ester by intracellular esterases releases an intermediate which is then processed by the targeted lytic enzyme to release the active inhibitor.

The compounds and methods of the invention are useful in therapeutic medical and veterinary applications, and are also useful in agrichemical applications such as control of insects or fungus.

In one aspect, the invention provides a conjugated compound that includes a first constituent that includes an enzymatic substrate; and a second constituent covalently linked to the first constituent. The second constituent includes an inhibitor moiety that, when released from the conjugated compound, inhibits the activity of an enzyme. The covalent linkage between the first and second constituents can be cleaved by the enzyme to release the inhibitor moiety. Optionally, the second constituent further includes at least a portion of a linking group, such that the first constituent is covalently linked to a linking group, which in turn is covalently linked to the inhibitor moiety. The linking group, if present, may be part of the first or second constituent, or it may be shared between them. Optionally, the second constituent self-fragments to yield the active inhibitor.

In one embodiment, the first constituent of the conjugated compound includes a carbohydrate moiety, and the second constituent contains an inhibitor that, when released from the conjugated compound, inhibits the activity of a glycosidase. The covalent linkage between the first and second constituents can be cleaved by the glycosidase to release the inhibitor moiety.

In another embodiment, the first constituent of the conjugated compound includes a polypeptide moiety, and the second constituent contains an inhibitor moiety that, when released from the conjugated compound, inhibits the activity of a protease. The covalent linkage between the first and second constituents can be cleaved by the protease to release the inhibitor moiety.

In yet another embodiment, the first constituent of the conjugated compound includes a kinase substrate; and the second constituent contains an inhibitor moiety that, when released from the conjugated compound, inhibits the activity of a kinase. The covalent linkage between the first and second constituents can be cleaved by the kinase to release the inhibitor moiety.

Optionally, the first and/or second constituent of the conjugated compound further includes a moiety that increases metabolic stability or facilitates cellular uptake. For example, the first and/or second constituent may be acetylated.

In a preferred embodiment, the conjugated compound contains a substrate for a glycosidase. For example, the first constituent can include a carbohydrate, and the inhibitor moiety can include mannostatin A or a derivative thereof.

In another aspect, the invention provides methods for making the conjugated compounds of the invention.

In yet another aspect, the invention provides methods for using the conjugated compounds of the invention. For example, prodrugs of the invention can be administered to a human or animal subject to treat a disease or condition, such as cancer, a precancerous condition, diabetes, hepatitis, a viral infection, a bacterial infection, a fungal infection, a genetic disorder, or a lysosomal storage disease. As another example, the conjugated compounds can be administered to a plant to function as an insecticide or fungicide. When administered to plants, the conjugated compounds can be sprayed onto the plants or administered in any other convenient way.

Unless otherwise specified, "a," "an," "the," and "at least one" are used interchangeably and mean one or more than one.

BRIEF DESCRIPTION OF THE DRAWINGS

FIG. 10 shows inhibition of human Golgi mannosidase II (HGMII) and human lysosomal mannosidase (HLM) using modified mannostatin A inhibitors.

FIG. 11 shows two procedures for combinatorial modification of a mannostatin inhibitor analog: (a) parallel combinatorial modification and (b) mix and split combinatorial modification.

DETAILED DESCRIPTION OF ILLUSTRATIVE EMBODIMENTS

Figure 1:
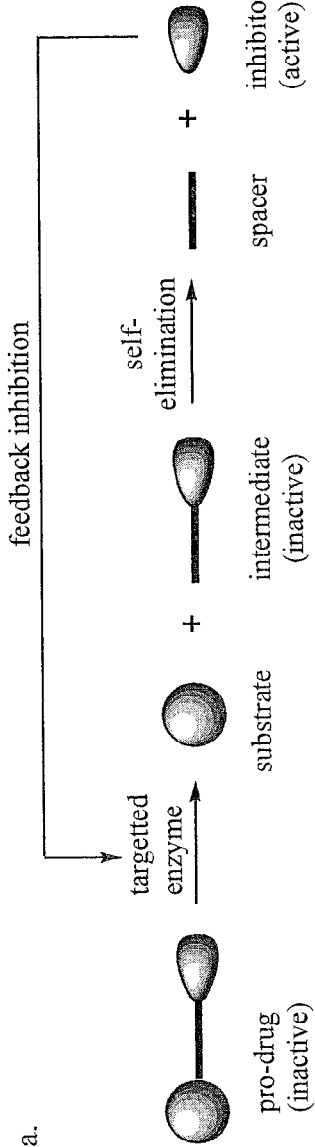
FIG. 1 shows a general strategy for the inhibition of enzymes by a feedback mechanism (Scheme 1a); and a feedback inhibitor for mannosidases (Scheme 1b).
Figure 1:
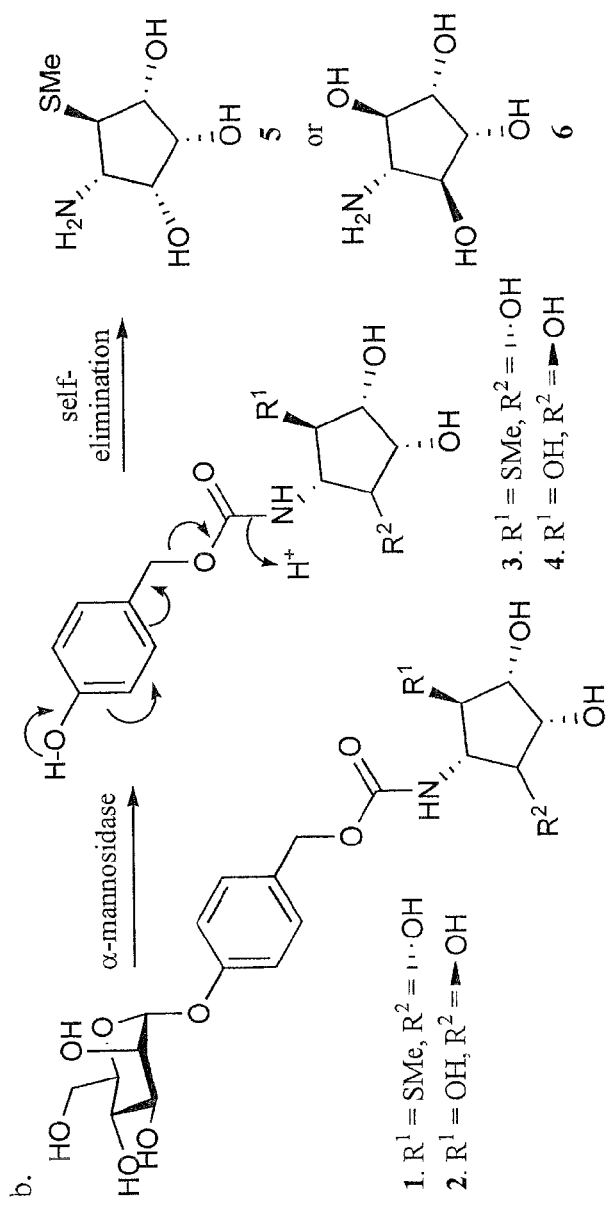

The present invention provides a compound and method for selective inhibition of a lytic enzyme. The compound of the invention is frequently referred to herein as a "prodrug". A novel prodrug is provided in the form of a conjugated compound that serves as a substrate for a lytic enzyme but also includes, as a direct or indirect cleavage product, an inhibitor of that enzyme. Contact between the prodrug and the lytic enzyme releases the inhibitor and thereby inhibits the activity of the lytic enzyme through the mechanism of feedback inhibition. The novel prodrug is expected to be effective for reducing the activity of the lytic enzyme in vitro and in vivo.

The invention is illustrated using inhibition of a glycosidase as an example. A glycosidase inhibitor is released by glycosidase-mediated hydrolysis of a prodrug, and subsequently inhibits the glycosidase that initiated the release of the inhibitor. It is expected that an analogous feedback prodrug approach can be applied for the design of selective inhibitors of many other classes of lytic enzymes.

A "lytic enzyme," as that term is used herein, refers generally to an enzyme that selectively cleaves a molecule. The molecule that is selectively cleaved by the lytic enzyme can be referred to generally as the substrate of the lytic enzyme. More particularly, however, the term "enzymatic substrate" as used herein is intended, unless otherwise stated, to refer to the particular portion of the conjugated compound that is needed for the compound to serve as an enzymatic substrate; it thus includes all or a portion of the first constituent (e.g., a carbohydrate, in the case of a lytic enzyme that is a glycosidase) and, optionally, a portion of the second constituent, such as all or a portion of the linking group as described in more detail below.

Lytic enzymes include, for example, glycosylases and glycosidases, proteases and peptidases, lipidases and lipases, kinases, and nucleases. There are numerous known natural inhibitors of glycosidases, and many synthetic glycosidase inhibitors as well, as described further below. Inhibitors of other lytic enzymes, such as protease inhibitors, kinase inhibitors, nuclease inhibitors, and lipase inhibitors are also well known and widely available commercially. The invention is not intended to be limited by the enzyme inhibitor used in the prodrug.

The prodrug of the invention includes a first constituent which includes an enzymatic substrate; and a second constituent group that includes an inhibitor moiety that, when released from the conjugated compound as a product of enzymatic cleavage, inhibits the activity of the enzyme that cleaved the prodrug. In the prodrug (i.e., the conjugated compound), the first constituent is covalently linked to the second constituent. The inhibitor, when present as a constituent of the conjugated compound, is in an inactive form; it does not inhibit the activity of the enzyme until released. Upon cleavage, the inhibitor moiety is released, thereby providing feedback inhibition of the enzymatic activity. The free inhibitor may be active (i.e., it may be able to inhibit the activity of the lytic enzyme) directly upon release, or the second constituent, after release, may constitute an intermediate that undergoes self-fragmentation to yield an active form of the inhibitor.

In one embodiment, the conjugated compound includes, as a first constituent, a carbohydrate moiety. A second constituent covalently linked to the first constituent is preferably an inhibitor moiety that, when released from the conjugated compound, inhibits the activity of a glycosidase. The covalent linkage between the first and second constituents is one that can be cleaved by the glycosidase to release the inhibitor. The inhibitor thus released may be immediately active to inhibit the glycosidase, or it may self-fragment to yield an active form of the inhibitor.

Likewise, in another embodiment, the first constituent includes a polypeptide moiety; and the second includes an inhibitor moiety that, when released from the conjugated compound, inhibits the activity of a protease. In yet another embodiment, the first constituent is selected to as provide a substrate for a kinase, and the second constituent includes an inhibitor moiety that, when released from the conjugated compound, inhibits the activity of the kinase. In other embodiments, the first constituent is selected to provide a substrate for a lipidase or a nuclease, and the second constituent includes an inhibitor moiety that, when released from the conjugated compound, inhibits the activity of the lipidase or nuclease.

Optionally, the conjugated compound includes, as part of the second constituent, at least a portion of a linking group, such that the first constituent is covalently linked to the linking group, which in turn is covalently linked to the inhibitor moiety. Preferred linking groups include 4-hydroxyl benzyl carbamate (O-linked), 4-aminobenzyl carbamate (N-linked), and their derivatives. However, the invention is not intended to be limited by the linking group used, and other linking groups, such as a "trimethyl lock" (O-linked), coumarin (O-linked), 2-hydroxyphenyl carbamate (O-linked), 2-hydroxypropyl carbamate (O-linked), 2-aminophenyl carbamate (N-linked), and N,N'-dimethylethylenediamine carbamate (N-linked) are included. After enzymatic cleavage to yield the second constituent, the second constituent may undergo self-fragmentation and the linking group may be released to yield an active form of the inhibitor.

Also optionally, the first or second constituent can be modified or derivatized to include a moiety that increases metabolic stability or facilitates cellular uptake, such as an acetyl group. One or more hydroxyl groups of the prodrug can be derivatized to yield an O-acetyl ester, which enhances delivery of the compound across the plasma membrane (Zhang et al., Proc. Natl. Acad. Sci. U.S.A. 1995, 92, 3323-3327). Other carbonoyloxy substitutions to the hydroxyl groups that confer improved medicinal properties are also envisioned, such as those that have been applied to the drug swainsonine (Dennis et al. Biochem. Pharmacol. 1993, 46, 1459-1466). Metabolic stability or uptake can also be improved, for example, by attaching a selected functional peptide to the drug, such as a cell permeable/drug delivery peptide, e.g., Arg9 (Ana Spec, San Jose Calif., Cat #61204), to the prodrug.

In a particularly preferred embodiment, the invention provides compounds and methods for selective inhibition of glycosidases. Glycosidase are involved in the biosynthesis of the oligosaccharide chains in the endoplasmic reticulum of the N-linked glycoproteins. Many glycosidases are known; some examples of glycosidases found in the human liver include mannosidases, glucosidases, galactosidases, fucosidases, xylosidases and hexosaminidases. Glycosidases can be α-glycosidases or β-glycosidases (e.g., α-mannosidase or β-mannosidase).

Over 100 naturally occurring glycosidase inhibitors have been isolated from plants and microorganisms. Many of them are alkaloids with a nitrogen heteroatom in the ring. These alkaloid glycosidase inhibitors are mainly classified into five structural classes: polyhydroxylated piperidines, pyrrolidines, indolizidines, pyrrolizidines and nortropanes. They can inhibit various glycosidases, such as glucosidases, glucosaminidases, galactosidases, mannosidases, fucosidases, sialidases and sucrases. They typically have broad inhibition activity relative to glycosidases.

Other glycosidase inhibitors, such as mannostatin A and mannostatin B, have a carbocyclic structure, which represents a significant departure from known alkaloid based inhibitors. The pentasubstituted cyclopentane (mannostatin A) and the corresponding sulfoxide of mannostatin A (mannostatin B, wherein the —$SCH_3$ is replaced by $S(O)CH_3$), were found to be potent competitive inhibitors of rat epididymal α-mannosidase. Mannostatin A was also found to be a potent inhibitor of Golgi processing mannosidase II (Tropea et al., Biochemistry 1990, 29, 10062).

Asano et al. (Glycobiology, 13(10), 2003, 93R-104R) have extensively reviewed glycosidase inhibitors. In the agrichemical field, glycosidase inhibitors include trehalase inhibitors, such as compounds in the validamycin family (e.g., validamycin A, validoxylamine A, α-homonojirimycin-7-O-β-D-glycopyranoside, trehazolin, salbostatin and causaurine-6-O-α-D-glucopyranoside) and chitinase inhibitors (e.g., allosamidin, argifin and argadin).

Antidiabetic agents include inhibitors of digestive α-glucosidase (e.g., acarbose, valiolamine, voglibose, nojirimycin, 1-deoxynojirimycin (DNJ), miglitol, salacinol and kotalanol) and glycogen phosphorylase inhibitors (e.g., 1,4-dideoxy-1,4-imino-D-arabinitol, isofagomine and fagomine). Antiviral agents include inhibitors of processing α-glucosidase I (e.g., N-butyl-DNJ, castanospermine, 6-O-butanoylcastanospermine, glycovir and N-nonyl-DNJ) and neuraminidase (sialidase) inhibitors (e.g., 2-deoxy-2,3-dehydro-N-acetyl-neuraminic acid (DANA), 2 deoxy-2,3-dehydro-N-trifluoroacetylneuraminic acid (FANA), 4-amino-4-deoxy-DANA, 4-deoxy-4-guanidino-DANA (zanamivir), 4-(acetylamino)-3-guanidinobenzoic acid, oseltamivir carboxylate, oseltamivir and peramivir).

Glycosidase inhibitors also hold much potential for molecular therapy of genetic disorders. For example, glycosphingolipid storage disease and other lysosomal storage diseases such as type 1 Gaucher disease can be treated using a glycosidase inhibitor. Inhibition of ceramide glucosyltransferase (glucosylceramide synthase), for example, can be used to effect substrate deprivation therapy for lysosomal storage diseases Inhibitors of ceramide glucosyltransferase (glucosylceramide synthase) inhibitors include N-butyl-1-deoxygalactonojirimycin (NB-DGJ), D-threo-1-phenyl-2-decanoylamino-3-morpholino-1-propanol (PDMP), D-threo-1-phenyl-2-palmitoilamino-3-pyrrolidino-1 propanol (P4), 4'-hydroxy-P4 (pOH—P4), 3',4'-ethylenedioxy-P4 (EtDO-P4) and N-(5-adamantane-1-yl-methoxypentyl)-DNJ (AMP-DNJ). Likewise, inhibition of lysosomal glycosidase can be used to effect chemical chaperone therapy for lysosomal storage diseases. Inhibitors of lysosomal glycosidase include 1-deoxygalactonojirimycin (DGJ), α-homogalactonojirimycin (HGJ), α-homoallonojirimycin (HAJ) and ββ-1-C-butyl-DGJ (CB-DGJ).

Additional examples of naturally occurring and synthetic enzyme inhibitors, including glycosidase inhibitors, can be found in de Melo et al., Tetrahedron 2006, 62, 10277-10302; Asano, Glycobiology 2003, 13, 93R-104R; Lillelund et al., Chem. Rev. 2002, 102, 515-553; Asano et al., Tetrahedron: Asymmetry 2000, 11, 1645-1680; Berecibar et al., Chem. Rev. 1999, 99, 779-844; von Itzstein et al., Curr. Med. Chem. 1997, 4, 185; Yuasa et al., Trends Glycosci. Glycotechnol., 2002, 14, 231-251; and Ekhart et al., Imisugars as Glycosidase Inhibitors Nojirimycin and Beyond; StUtz, A. E., Ed.; WILEY-VCH: New York, 1999; pp. 253-390. Other examples of modified inhibit Mannostatin A, as well as derivatives or modifications thereof, represents an exemplary glycosidase inhibitor for use in the prodrug of the invention. Mannostatin A is released by glycosidase-mediated hydrolysis of the prodrug, which subsequently inhibits the glycosidase that initiated the release of the inhibitor. Derivatives and modifications of mannostatin A (or any other naturally occurring inhibitor) include any chemically or enzymatically modified inhibitor. Preferably, modified mannostatins retain the basicity of the primary amine as well as the neighboring cis-diol, each of which has been suggested as important for inhibitory activity (King et al., J. Am. Chem. Soc 1994, 116, 562-570; Ogawa et al., Bioorg. Med. Chem. Lett, 1999, 9, 1499-1504; Ogawa et al., Bioorg. Med. Chem. Lett, 2000, 10, 1047-1050; Kleban et al., Chem. Bio. Chem. 2001, 2, 365-368; Boss et al., Org. Lett., 2000, 2, 151-154; Popowycz et al., Bioorg Med. Chem. Lett, 2001, 121, 2489-2493; Ogawa et al., Eur. J. Org. Chem. 1998, 1929-1934). Synthetic studies on mannostatin A and some of its derivatives have been reported by King et al. (J. Am. Chem. Soc., 1994, 116, 562-570). Exemplary modifications include, but are not limited to, substitution of hydrogen or other functional group on the inhibitor structure. For example, in the case of mannostatin A, modifications include replacement of the methyl thioether group (—S—$CH_3$; also written as —S-Me, wherein Me refers to a methyl group) with a phenyl thioether (—S-Ph, wherein Ph refers to a phenyl group) or any other aliphatic or aromatic thioether. The thioether functionality of mannostatin A can likewise be replaced by an ether, for example to create the O-alkyl or O-aryl derivatives, such as the —O—$CH_3$ and O-Ph derivatives of mannostatin A.

Substitution of the methyl thioether with other sulfur containing substituents, such as a sulfoxide as in mannostatin B, is also contemplated. Likewise, other substitutions are envisioned; for example, the primary amine on mannostatin A (—NH$_2$) can be replaced by a secondary or tertiary amine of interest. Typically, the amine is the site for covalent attachment of the second constituent of the prodrug, thereby forming the substrate that is cleavable by the enzyme. Thus, linkers designed for use in the mannostatin A prodrug are typically attached to the amine group of mannostatin A. Depending on where the cleavage site is positioned in the linker; the inhibitor that is released after hydrolysis may be a derivatized form of mannostatin A. The derivatized form may be an active inhibitor, or it may go through additional self-fragmentation to yield the active inhibitor.

As previously noted, the fact that the prodrug of the invention contains a linkage that is cleavable by the enzyme to be inhibited effectively increases selectivity of the inhibitor. The linkage is selected so as to supply a substrate for the enzyme, and selectivity of the inhibitor is thereby improved because of the exquisite selectivity of enzymes for their substrates. The feedback inhibition process insures that the targeted enzyme is in close proximity to the released inhibitor. The effective concentration of the targeted enzyme is increased in the vicinity of the released inhibitor. Thus, delivery of the inhibitor via the prodrug of the invention can effectively increase the selectivity of an otherwise lower selectivity inhibitor. Selectivity can be further increased by using, when available, an inhibitor that has been shown to have high innate selectivity for the enzyme to be inhibited.

There are many ways to design ligands, in particular enzyme inhibitors, which are expected to exhibit improved binding to and/or selectivity for an enzyme of interest, such as a selected glycosidase. The three dimensional structure of the enzyme, if known, can be displayed in a modeling environment, such as Insight II. Binding sites are identified, for example by inspection, or using a computer-aided process, and inhibitors that target those sites can be designed. Design of potential inhibitors is facilitated if the structure of one or more protein-inhibitor complexes is known.

Candidate inhibitors can be identified by searching through databases such as the Cambridge Structural Database (Allen et al., Acc. Chem. Res., 16, 148 (1983); Allen et al., Acta Crystallogr., B35, 2331 (1979)) and identifying those that fit into the active site. The molecular structures in these databases are known to exist and typically represent low-energy conformations. However, this approach does not address the issue of conformational flexibility. The conformation of an inhibitor bound to the enzyme may be different from its conformation in the crystal structure conformation (Hambley et al., J. Am. Chem. Soc., 108, 2103 (1986)). Additionally, the databases contain a finite number of structures. Moreover, the number and variety of structures is limited by the size of the database used.

Another approach utilizes a library of structural fragments, rather than complete inhibitor candidates. The molecular fragments are positioned into the binding site of the enzyme so that they make favorable contacts with atoms in the enzyme. For example, they can be positioned to facilitate hydrogen bonding and hydrophobic interactions between the fragments and the enzyme. The fragments are then connected by suitable spacer fragments, as necessary, to form a single molecule. An example of computer program useful in carrying out the fragment approach is the LUDI method (e.g., the LUDI module from Insight II; see also Böhm, J. Comp. Aided Molec. Design, 6, 69 (1992); Böhm, J. Comp. Aided Molec. Design, 6, 593-606 (1992).

Examples of modified inhibitors designed with the computer program LUDI (Insight II modeling program; Accelrys), using mannostatin A as the basic structure, are described in Example II. Linkage of an aromatic substituent to the primary amine in mannostatin A, as described, for example, in Example II, may increase selectivity of mannostatin A for human α-Golgi mannosidase II, a known target for anti-metastasis therapy.

The invention further includes a pharmaceutical composition that contains the prodrug of the invention. The prodrug of the invention is readily formulated as a pharmaceutical composition for veterinary or human use. The pharmaceutical composition optionally includes excipients or diluents that are pharmaceutically acceptable as carriers and compatible with the prodrug. The term "pharmaceutically acceptable carrier" refers to a carrier(s) that is "acceptable" in the sense of being compatible with the other ingredients of a composition and not deleterious to the recipient thereof or to the live attenuated virus. Suitable excipients include, for example, water, saline, dextrose, glycerol, ethanol, or the like and combinations thereof. In addition, if desired, the pharmaceutical composition may contain minor amounts of auxiliary substances such as wetting or emulsifying agents, pH buffering agents, salts, and/or adjuvants which enhance the effectiveness of the immune-stimulating composition. For oral administration, the prodrug can be mixed with proteins or oils of vegetable or animal origin. Methods of making and using such pharmaceutical compositions are also included in the invention.

The invention also includes methods of using the prodrug for the treatment a disease or condition that can be treated by inhibiting the activity of a lytic enzyme, such as a glycosidase. An example of such a disease or condition is cancer or a precancerous condition such as dysplasia or hyperplasia. Glycosidase inhibitors can also be used for treating diabetes, hepatitis, viral (HIV, influenza) infections, bacterial infections, fungal infections, genetic disorders, and lysosomal storage diseases.

The pharmaceutical composition of the invention can be administered to any subject including humans and domesticated animals (e.g., cats and dogs). Dosage amounts, schedules for administration and the like for the pharmaceutical composition of the invention are readily determinable by those of skill in the art. The pharmaceutical composition can be administered to the subject using any convenient method, preferably parenterally (e.g., via intramuscular, intradermal, or subcutaneous injection), via oral or nasal administration, or via perfusion at the target area. The useful dosage to be administered will vary, depending on the type of animal to be treated, its age and weight, and mode of administration.

Methods of making prodrug as generally described herein are also encompassed by the invention.

EXAMPLES

The present invention is illustrated by the following examples. It is to be understood that the particular examples, materials, amounts, and procedures are to be interpreted broadly in accordance with the scope and spirit of the invention as set forth herein.

Example I

Selective Inhibition of Glycosidases by Feedback Prodrugs

We report here a general approach for the design and synthesis of selective glycosidase inhibitors based on feedback inhibition. Feedback inhibition is a mechanism in which a biosynthetic pathway regulates itself through inhibition of the first committed step in the pathway by a down stream or final product (Pardee et al., Gene 2003, 321, 17). Although this type of inhibition is widely used in nature, it has not been exploited for the design and synthesis of selective therapeutics. The feedback inhibition prodrugs described here are composed of an inhibitor that is modified by a linker that renders them inactive (Scheme 1a; FIG. 1). The linker, in turn, is attached to a glycoside that can be hydrolyzed by a targeted glycosidase. The resulting intermediate is designed in such a way that it will undergo self-fragmentation to release the active inhibitor. Subsequently, the inhibitor will inhibit the enzyme that initiated its release. The attraction of this approach is that the inhibitor will only be released at the site of the enzyme. Selectivity is achieved due to the exquisite selectivity of glycosidases for their substrates. Furthermore, the release of the inhibitor is terminated when a sufficient quantity of the inhibitor is released. The remaining pool of prodrug will, however, be activated when active enzyme reappears thereby approximating conditions of continuous infusion.

Results and Discussion

Compound 1 is a feedback inhibitor that is designed to selectively target α-mannosidases. It is composed of mannostatin A (Berecibar et al., Chem. Rev. 1999, 99, 779) which is a potent inhibitor of α-mannosidases and has garnered attention as a lead compound for cancer drug development (Scheme 1b; FIG. 1). The amino group of mannostatin A is modified by a 4-hydroxyl benzyl carbamate, which in turn is linked to an α-mannoside. The acylation of the amino group of mannostatin A renders the compound inactive for inhibition of mannosidases (King et al., J. Am. Chem. Soc. 1994, 116, 562). However, an α-mannosidase can hydrolyze the glycosidic linkage resulting in the formation of intermediate 3, which will self fragment (de Groot et al., J. Org. Chem. 2001, 66, 8815) to give mannostatin A (5). The active mannostatin A will then inhibit the α-mannosidase that initiated its release, terminating the enzymatic reaction. On the other hand, the enzymatic hydrolysis of compound 2 will release aminocyclopentitetrol 6, which is not an inhibitor of an α-mannosidase (Ogawa et al., Bioorg. Med. Chem. Lett. 2000, 10, 1047) and therefore this reaction is expected to proceed to completion.

Figure 2:
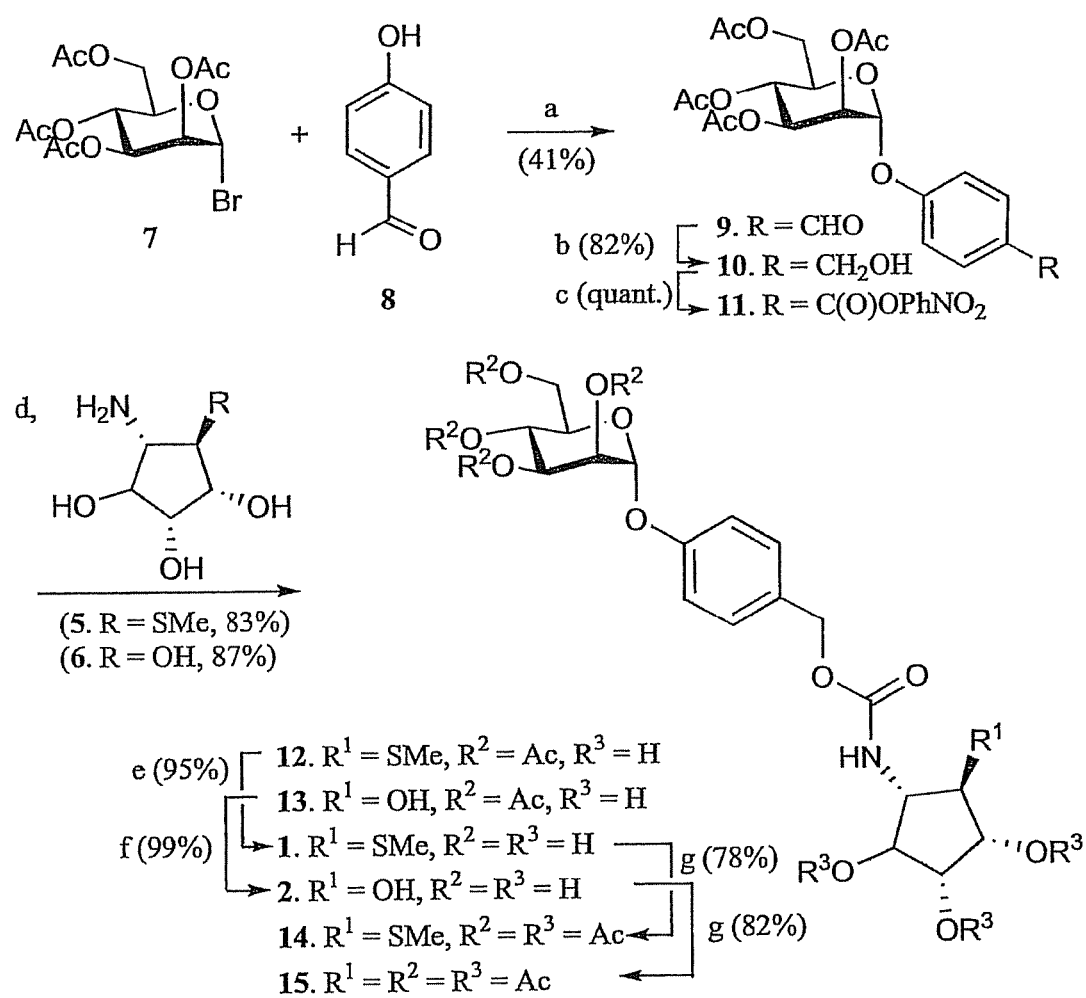
FIG. 2 shows the chemical synthesis of compound 1, a feedback inhibitor that is designed to selectively target α-mannosidases, and compound 2 (Scheme 2—Reagents and conditions: a) Ag$_2$O, CH$_3$CN, Δ, 1 hr; b) NaBH$_4$, silica, CHCl$_3$, i-PrOH; c) pyridine, DCM, 18 hrs; d) Et$_3$N, DMF 18 hrs; 3) NH$_3$ in MeOH; 1) NH$_2$NH$_2$ H$_2$O, MeOH, 0° C., 5 hrs, g) Ac$_2$O, pyridine).

The synthesis of compounds 1 and 2 is summarized in Scheme 2 (FIG. 2). Coupling of bromo 2,3,4-6-tetra-O-acetyl-α-D-mannose 7 with p-hydroxybenzaldehyde 8 using silver(I)oxide as the promoter in refluxing acetonitrile gave 9 in a modest yield. The aldehyde moiety of 9 was reduced with NaBH$_4$ to give 10, which was converted into activated intermediate 11 by reaction with 4-nitrophenyl chloroformate. This compound was immediately reacted with 5 and 6 to afford compounds 12 and 13, respectively. The acetyl esters of 12 and 13 were cleaved by treatment with ammonia or hydrazine in methanol to give the targeted compounds 1 and 2, respectively.

Figure 3:
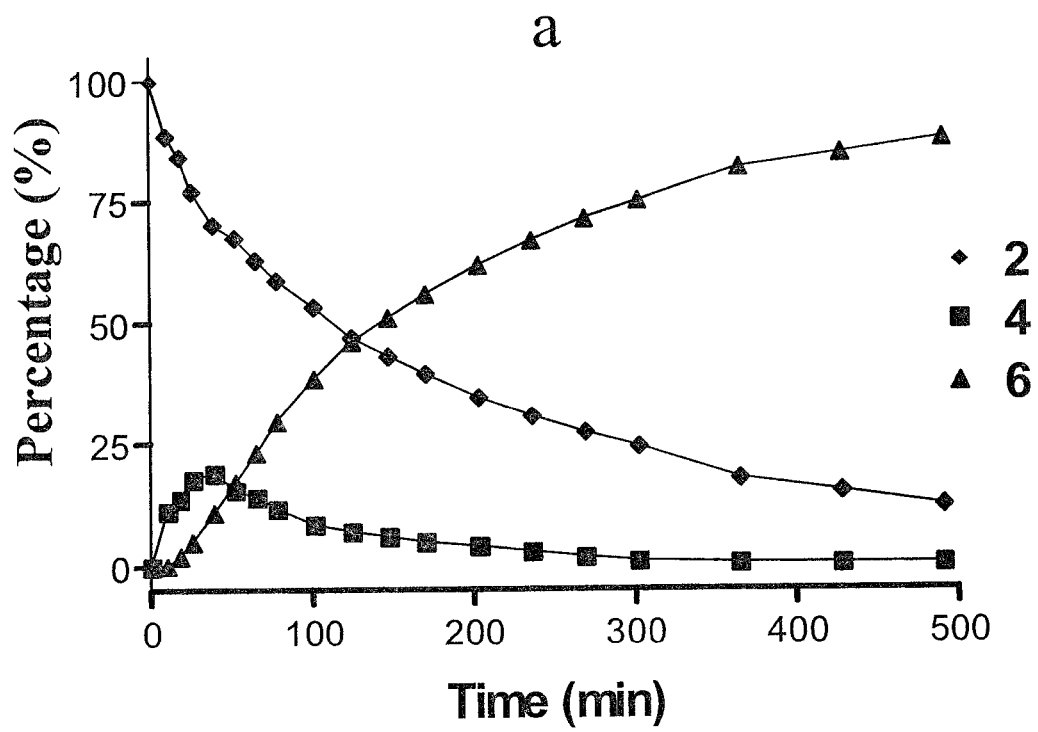
FIG. 3a shows release of prodrug 2 by human lysosomal mannosidase. HLM (20 mU) was added to a solution of prodrug 2 (0.08 μM) in a deuterated sodium acetate buffer (100 mM, pH, 5.6, 0.2 mL) and the enzymatic cleavage was monitored by $^1$H NMR (600 MHz).
FIG. 3b shows release of prodrug 1 by human lysosomal mannosidase. HLM (20 mU) was added to a solution of prodrug 1 (0.08 μM) in a deuterated sodium acetate buffer (100 mM, pH, 5.6, 0.2 mL) and the enzymatic cleavage was monitored by $^1$H NMR (600 MHz).
Figure 3:
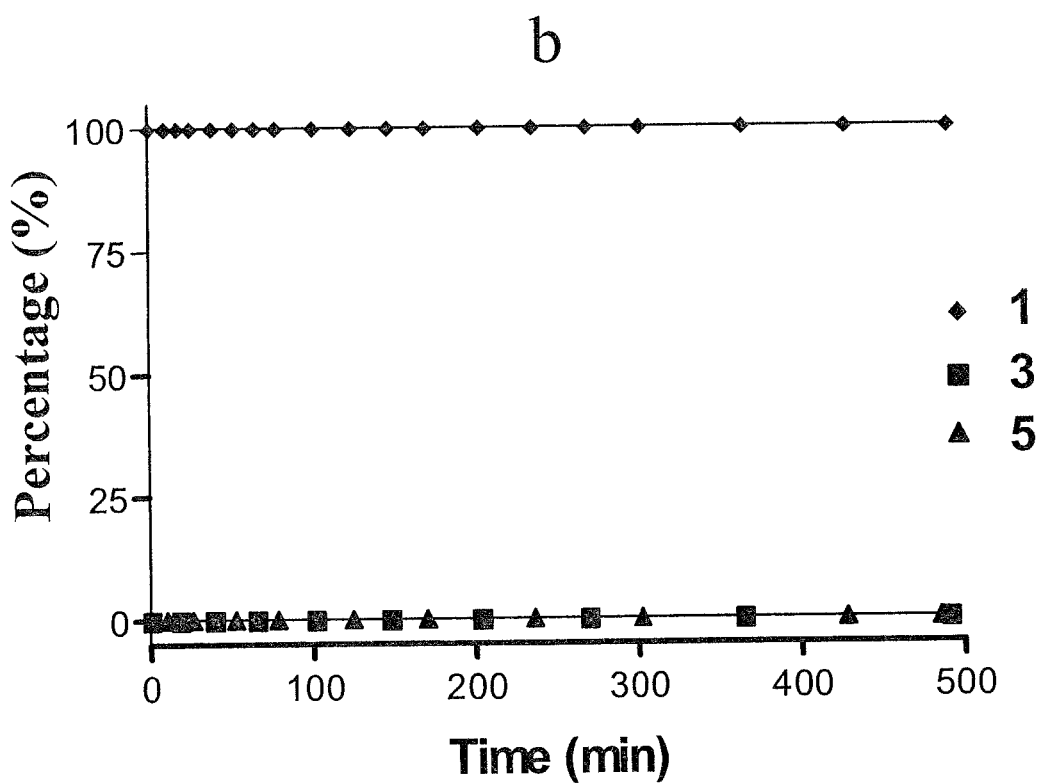

The enzymatic cleavage of 1 and 2 by human lysosomal mannosidase (HLM) was monitored by $^1$H NMR (600 MHz) (Wilson et al., Org. Lett. 1999, 1, 443) Thus, HLM (20 mU) was added to a solution of 1 or 2 (80 nmol) dissolved in a deuterated sodium acetate buffer (100 mM, pH 5.6, 0.2 mL). The progress of the reaction was monitored by the integration of key signals of the starting material, the intermediate and final product. As can be seen in FIG. 3a, HLM hydrolyzed 2 producing intermediate 4, which self fragmented to aminocyclopentitetrol 6. Compound 6 is not an inhibitor of HLM and as a result the enzymatic conversion progressed to completion. On the other hand, virtually no hydrolysis was observed when 1 was treated with HLM (FIG. 3b). In this case, the released mannostatin A (5) inhibits HLM terminating further hydrolysis of 1. Mannostatin A is a potent inhibitor of retaining α-mannosidases ($K_i$=90 nM, HLM) (Li et al., Chem. Bio. Chem. 2004, 5, 1220) and thus the release of low concentrations of the active compound is sufficient to abolish enzyme activity. Indeed, the addition of 4-methylumbelliferyl α-D-mannopyranoside did not result in the release of fluorescence methylumbelliferone, demonstrating that the mannosidase was inhibited by the released mannostatin A.

Compounds 1 and 2 were subjected to an α-glucosidase, α-fucosidase and α-galactosidase. As expected, these enzymes did not initiate the release of the compounds 5 and 6, demonstrating that they have exquisite selectivity for α-mannosidases (data not shown). Additionally, treatment of compound 1 with cell lysate in the presence of swainsonine and kifunensine did not lead to decomposition, indicating that proteases or other enzymes do not decompose the prodrug.

Next, the pH dependence of the self-fragmentation of intermediates 3 and 4 was investigated. It is well known that different organelles have different pH values. For example, lysosomes are significantly more acidic than the Golgi apparatus. Golgi mannosidase II has been identified as a target for anti-metastatic therapy (Goss et al., Clin. Cancer Res. 1995, 1, 935; Elbein, FASEB J. 1991, 5, 3055), whereas inhibition of lysosomal mannosidase leads to the phenotype of lysosomal storage disease. It was expected that intermediates 3 and 4 will fragment significantly faster in neutral as opposed to acidic conditions, providing a basis for some selectivity for Golgi-over the lysosomal mannosidase. Thus, compound 2 (0.4 mM) in sodium acetate buffers of different pH was treated with a large quantity (7 Units/mL) of Jack Bean α-mannosidase (JBM) to completely convert the prodrug into intermediate 4. Subsequently, the decomposition of 4 was monitored by $^1$H NMR by integration of key signals of the intermediate and final product. As can be seen in Table 1, the decomposition of 4 is significantly faster at more basic pH and elevated temperatures. These results can easily be rationalized by assuming that at a higher pH a large proportion of the intermediate is in the phenoxide form, which decomposes significantly faster than the analogues phenol. The results of these experiments indicate that in a compartment such as the medial Golgi, which has a pH close to neutral, the decomposition of the intermediate will occur in minutes, which is probably fast enough for rebinding of the inhibitor.

TABLE 1 pH-dependence of half-lives of self-fragmentation of 2

| | pH | | | | | |
|---|---|---|---|---|---|---|
| | 4.0 | 4.5 | 5.0 | 5.5 | 6.0 | 6.5 |
| 37° C. (min) | 480 | 270 | 100 | 45 | 16 | 9 |
| 25° C. (min) | 2800 | — | — | — | — | 45 |

Incubating of prodrug 2 (0.08 μM) and Jack Bean mannosidase (1.4 U/mL) in deuterated 0.2M phosphate/0.1M citrate buffer (0.2 mL) at 37° C. or 25° C. in a NMR tube and running $^1$H NMR spectra over time on a 600 MHz spectrometer.

For many applications, compounds such as 1 need to be cell permeable to inhibit intracellular glycosidases. Analysis of fetal calf serum (FCS), which is often used for culturing cells, revealed that it contains a significant amount of mannosidase activity. Thus, these mannosidases can unmask mannostatin A, which can then pass through the cell membrane to inhibit intracellular mannosidases. It was anticipated that the O-acetylation of 1 and 2 to give 14 and 15, respectively would considerably improve the metabolic stability of the prodrug. Furthermore, it has been shown that O-acetylation of saccharides can facilitate cellular uptake (Sarkar et al., Proc. Natl. Acad. Sci. USA 1995, 92, 3323). Subsequently, intra-cellular esterases can cleave the acetyl esters revealing the saccharide, which can then interfere in the biosynthesis of oligosaccharides. FCS exhibits only very low levels of esterase activity therefore improving extra-cellular stability of acetylated carbohydrates. Thus, it was anticipated that compound 14 would be easily taken-up by cells and subsequent deacetylation by intracellular esterases would reveal 1, which can then be hydrolyzed by an α-mannosidase, initiating the release of mannostatin A.

Figure 4:
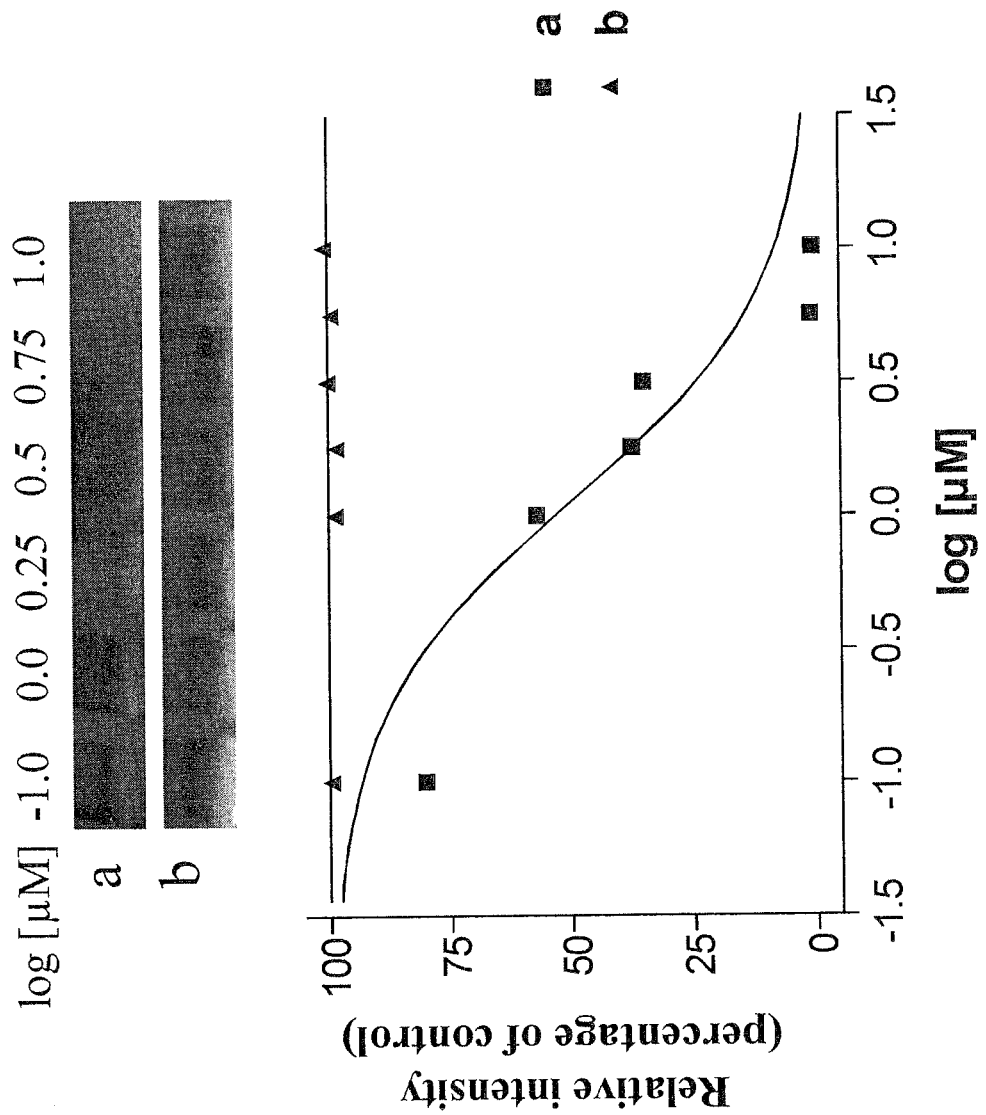
FIG. 4 shows inhibition of polylactosamine formation by compounds 14 and 15. MDAY-D2 cells were cultured for 2 days in the absence (control) or presence of different concentrations of compounds 14 (a) or 15 (b). Cellular proteins (10 μg) were subjected to SDS-PAGE and polylactosamine was visualized using a fluorescein labeled L-PHA lectin (upper part figure). Fluorescence bands were scanned by laser beam densitometry, and the relative intensity depicted (lower part figure).

In order to investigate whether 14 possesses intracellular activity, it was subjected to MDAY-D2 cells and the disappearance of polylactosamine monitored. It is known that the metastatic MDAY-D2 lymphoma cell line over-expresses the enzyme N-acetyl glucosaminyltransferase V (GnTV) (Goss et al., Clin. Cancer Res. 1995, 1, 935). This enzyme adds an additional β1-6-linked N-acetyl glucosamine moiety to Asn-linked oligosaccharides, which is subsequently extended by a polylactosamine chain. This increased branching has been observed in human breast, colon and skin carcinomas and has been correlated with invasive and metastatic potential. Inhibition of the mannose trimming enzyme human Golgi α-mannosidase II (HGMII), which acts late in the N-glycan processing pathway, provides one route to blocking additional branching of N-linked oligosaccharides (Goss et al., Clin. Cancer Res. 1995, 1, 935). In this case, the biosynthetic precursor for GnTV is not formed and hence the polylactosamine chain cannot be appended. Thus, in order to investigate whether the acetylated prodrugs can inhibit intra-cellular Golgi mannosidase MDAY-D2 lymphoma cells were cultured in the presence of different concentrations of 14 and 15 for two days. Subsequently, the presence of polylactosamine linked to proteins was determined by analyzing cell lysates by Western blotting using a fluorescein labeled PHA lectin (Dennis et al., Cancer Res. 1990, 50, 1867). Interestingly, at a concentration of 1 µM of 14, a 50% reduction in fluorescein labeling was observed, whereas compound 15 did not display any inhibitory activity (FIG. 4).

Conclusion

It is now well established that glycosidases are involved in many vital cellular functions and it has been realized that inhibitors of these enzymes may find application as therapeutic agents for many different diseases. In this respect, inhibitors of pancreatic α-amylase, such as Arcarbose, Voglibose and Miglitol, have been introduced for the treatment of diabetes. Furthermore, compounds such as Zamamivir and Oseltamivir (Tamiflu) have been developed as inhibitors of neuramidase for the treatment of flu. Despite these successes, it has been difficult to develop safe and efficacious glycosidase inhibitors for the treatment of many other diseases. A major problem of many natural and synthetic glycosidase inhibitors is that they inhibit other glycosidases, which may lead to serious side effects. More selective inhibitors may be obtained by carefully designed structure-activity relationship studies in combination with a better understanding of the mechanism of action of glycosidases. This approach is, however, complicated by the fact that of the hundreds of mammalian glycosidases only a small number have been cloned and over-expressed.

Glycosidases are enzymes that play crucial roles in the biosynthesis of glycoproteins. Inhibitors of these enzymes have garnered attention as lead compounds for drug discovery. However, progress in drug discovery has been hampered by the difficulties of designing selective inhibitors. A feedback prodrug approach, whereby a glycosidase inhibitor is released by the targeted glycosidase, offers an attractive strategy for enhancing the selectivity of a glycosidase inhibitor. Another advantage of this type of prodrug is that only that amount of compound is released for complete inhibition of the targeted enzyme.

The advantageous properties of the novel prodrugs are demonstrated by the chemical synthesis and biological evaluation of compounds 1 and 2. Compound 1 is composed of mannostatin A, which is modified by a 4-hydroxyl benzyl carbamate, which in turn is linked to an α-mannoside. Hydrolysis of the mannoside of 1 by an α-mannosidase gave an intermediate which self fragmented to release mannostatin A (5). The resulting mannostatin potently inhibited the α-mannosidase that initiated its release, terminating further release. On the other hand, hydrolysis of the mannoside of 2 resulted in the release of aminocyclopentitetrol 6, which is not an inhibitor of α-mannosides. As expected, the hydrolysis of 2 progressed to completion. The selectivity of the process was demonstrated by the inability of α-glucosidase, α-fucosidase and α-galactosidase to cleave the prodrugs. Finally, an acetylated derivative of 1 was shown to be cell permeable and after deacetylation by intracellular esterases and release of mannostatin A, Golgi α-mannosidase II was inhibited as demonstrated by the disappearance of protein-linked polylactosamine.

It is to be expected that chemical modification of a lead compound in combination with a feedback prodrug formulation may make it easier to develop glycosidase inhibitors as safe therapeutics. In addition, the feedback prodrug approach will not be limited to glycosidase targets and it is to be expected that it can also be applied to the design of inhibitors of other classes of enzymes such as proteases and kinases.

Materials and Methods

General synthetic procedures. All reactions were carried out under a positive pressure of argon, unless otherwise noted. All chemicals were purchased from commercial suppliers and used without further purification, unless otherwise noted. All solvents employed were of reagent grade and dried by refluxing over appropriate drying agents. Column chromatography was performed on silica gel 60 (EM Science, 70-230 mesh). Reactions were monitored by TLC on Kieselgel 60 F254 (EM Science) and the compounds were detected by examination under UV light and visualized by dipping the plates in a cerium sulfate-ammonium molybdate solution followed by heating. $^1$H NMR and $^{13}$C NMR spectra were recorded with a Varian Inova 300 spectrometer and a Varian Inova 600 spectrometer equipped with Sun workstations. Chemical shifts are reported in parts per million (ppm) downfield from tetramethylsilane. Data are presented as follow: Chemical shift multiplicity: s=singlet, d=doublet, t=triplet, dd=double of doublet, m=multiplet and/or multiple resonances, b=broad, integration, coupling constant in Hertz (Hz), assignments: "m" for mannose, "a" for aromatic, and "d" for mannostatin A or cyclopentanetetrol. High resolution positive ion matrix assisted laser desorption ionization time of flight (MALDI-TOF) mass spectra were recorded using an Applied Biosystems MALDI instrument by using gentisic acid as a matrix.

4-(2,3,4,6-tetra-O-acetyl-α-D-mannopyranosyloxy)-benzaldehyde (9). A mixture of tetra-O-acetyl-α-D-mannopyranosyl bromide (2.40 g, 5.84 mmol), 4-hydroxybenzalhyde (1.43 g, 11.7 mmol) and silver(I)oxide (1.76 g, 7.59 mmol) in acetonitrile (30 ml) in the dark was heated under reflux for 1 h. Then, the reaction mixture was filtered through celite, the filtration was concentrated in vacuo, and the residue was purified by flash column chromatography over silica (1:2

EtOAc/hexanes) to give 7 (1.08 g, 41%) as a colorless syrup. $R_f$=0.55 (1:1 hexanes/EtOAc). $^1$H NMR (CDCl$_3$, 300 MHz) δ 2.00, 2.03, 2.04, 2.19 (4×s, 12H, 4×CH$_3$, Ac), 3.98-4.12 (m, 2H, H-m5, m6α), 4.25 (dd, 1H, J=5.6, 12.2 Hz, H-m6β), 5.36 (t, 1H, J=10.1 Hz, H-m4), 5.44 (dd, 1H, J=1.8, 3.4 Hz, H-m2), 5.53 (dd, 1H, J=3.4, 10.1 Hz, H-m3), 5.62 (d, 1H, J=1.8 Hz, H-m1), 7.21 (d, 2H, J=8.8 Hz, H-a2), 7.85 (d, 2H, J=8.8 Hz, H-a3), 9.91 (s, 1H, COH). $^{13}$C NMR (CDCl$_3$, 75 MHz) δ 20.80 (CH$_3$), 20.83 (CH$_3$), 20.85 (CH$_3$), 21.0 (CH$_3$), 62.2 (C-m2), 65.9 (C-m3), 68.8, 69.3, 69.8 (C-m6, m4, m5), 95.7 (C-m1), 116.8 (C-a2), 131.9 (C-a4), 132.0 (C-a3), 160.3 (C-a1), 169.8 (MeCO), 170.1 (2 carbons, MeCO×2), 170.6 (MeCO), 190.9 (PhCOH). MALDI-TOF MS (m/z) calcd for C$_{21}$H$_{24}$O$_{11}$Na: 475.1216; found 475.1298 [M+Na]$^+$.

[4-(hydroxymethyl)phenyl]-(2,3,4,6-tetra-O-acetyl-α-D-mannopyranoside) (10). To a colded suspension (0° C.) of 9 (0.407 g, 0.9 mmol) and silica gel (0.6 g) in CHCl$_3$ (8 ml) and i-PrOH (2 ml) was added sodium borohydride (0.151 g, 4.0 mmol). The reaction mixture was stirred at 0° C. for 1 h, and then allowed to warm to room temperature, after which it was filtered over a pad of celite which was washed with CH$_2$Cl$_2$ (20 ml). The combined filtrates were concentrated in vacuo, and the residue was purified by flash column chromatography over silica (1:1 EtOAc/hexanes) to give 10 (0.340 g, 82%) as a colorless syrup. $R_f$=0.25 (1:1 hexanes/EtOAc). $^1$H NMR (CDCl$_3$, 300 MHz) δ 2.00, 2.01, 2.03, 2.18 (4×s, 12H, 3×CH$_3$, Ac), 2.85 (s, 1H, OH), 4.00-4.11 (m, 2H, H-m5, m6α), 4.25 (dd, 1H, J=5.5, 12.3 Hz, H-m6β), 4.59 (s, 2H, PhCH$_2$), 5.34 (t, 1H, J=10.1 Hz, H-m4), 5.42 (dd, 1H, J=1.8, 3.4 Hz, H-m2), 5.49 (d, 1H, J=1.6 Hz, H-m1), 5.53 (dd, 1H, J=3.5, 10.1 Hz, H-m1), 7.04 (d, 2H, J=8.7 Hz, H-a2), 7.27 (d, 2H, J=8.7 Hz, H-a3). $^{13}$C NMR (CDCl$_3$, 75 MHz) δ 20.68 (CH$_3$), 20.71 (2×CH$_3$), 20.9 (CH$_3$), 62.2 (C-m2), 64.5 (PhCH$_2$), 66.0 (C-m3), 69.0, 69.2, 69.4 (C-m6, m4, m5), 95.9 (C-m1), 116.6 (C-a2), 128.5 (C-a3), 135.8 (C-a4), 155.0 (PhCH$_2$), 169.9 (MeCO), 170.08 (MeCO), 170.11 (MeCO), 170.7 (MeCO). MALDI-TOF MS (m/z) calcd for C$_{21}$H$_{26}$O$_{11}$Na: 477.1373; found 477.1275 [M+Na]$^+$.

[4-(4-nitro-phenoxycarbonyloxymethyl)phenyl]-(2,3,4,6-tetra-O-acetyl-α-D-mannopyranoside) (11). To a solution of 10 (0.265 g, 0.583 mmol) and 4-nitrophenyl chloroformate (0.294 g, 1.458 mmol) in CH$_2$Cl$_2$ (8 ml) was added two drops of pyridine. The reaction mixture was stirred for 18 h at r.t., after which it was concentrated in vacuo, purified by flash column chromatography over silica (1:2 to 1:1 EtOAc/hexanes) to give 11 (0.325 g, 90%) as a white solid. $R_f$=0.45 (1:1 hexanes/EtOAc). $^1$H NMR (CDCl$_3$, 300 MHz) δ 2.03, 2.04, 2.06, 2.21 (4×s, 12H, 4×CH$_3$, Ac), 4.04-4.11 (m, 2H, H-m5, m6α), 4.28 (dd, 1H, J=5.7, 12.8 Hz, H-m6β), 5.24 (s, 2H, PhCH$_2$), 5.38 (t, 1H, J=10.0 Hz, H-m4), 5.44 (dd, 1H, J=1.9, 3.5 Hz, H-m2), 5.55 (d, 1H, J=1.9 Hz, H-m1), 5.56 (dd, 1H, J=3.5, 10.0 Hz, H-m3), 7.12 (d, 2H, J=8.7 Hz, H-a2), 7.37 (d, 2H, J=9.2 Hz,), 7.40 (d, 2H, J=8.7 Hz, H-3a), 8.27 (d, 2H, J=9.2 Hz, O$_2$N-Ph-H). $^{13}$C NMR (CDCl$_3$, 75 MHz) δ 20.88 (CH$_3$), 20.90 (CH$_3$), 20.91 (CH$_3$), 21.1 (CH$_3$), 62.3 (C-m2), 66.1 (C-m3), 69.0, 69.5 & 69.6, 70.7 (C-m6, m4, m5), 77.4 (PhCH$_2$), 96.0 (C-m1), 117.0 (C-a2), 122.0 (C-2 of PhNO$_2$), 125.5 (C-3 of PhNO$_2$), 129.0 (C-a3), 130.8 (C-a4), 145.6 (C-4 of PhNO$_2$), 152.6 (oco$_2$), 155.7 (C-a1), 156.4 (C-1 of PhNO$_2$), 169.9 (MeCO), 170.18 (MeCO), 170.22 (MeCO), 170.7 (MeCO). MALDI-TOF MS (m/z) calcd for C$_{28}$H$_{29}$NO$_{15}$Na: 642.1435; found 642.1421 [M+Na]$^+$.

1D-(1,2,3,4/5)-4-[4-(2,3,4,6-tetra-O-acetyl-α-D-mannopyranosyloxy)-benzyloxycarbonyl]amino-5-(methylsulfanyl)cyclopentane-1,2,3-triol (12). To a suspension of 11 (36.3 mg, 0.0585 mmol) and mannostatin A hydrochloride (12.6 mg, 0.0585 mmol) in DMF (4 ml) was added Et$_3$N (32.6 μl, 0.234 mmol). After stirring the reaction mixture for 18 h at r.t., it was concentrated in vacuo. The residue was purified by flash chromatography over Iatrobeads (2-4% MeOH in CH$_2$Cl$_2$) to give 12 (32 mg, 83%) as white solid. $R_f$=0.70 (1:9 MeOH/CH$_2$Cl$_2$). $^1$H NMR (10% CD$_3$OD/CDCl$_3$, 300 MHz) δ 1.97 (s, 6H, 2×CH$_3$, Ac), 1.99 (s, 3H, Ac), 2.13 (s, 6H, CH$_3$, Ac, SCH$_3$), 2.81 (b, 1H, H-d5), 3.80 (b, 2H, H-d1, d4), 3.96-4.05 (m, 4H, H-d2, d3, m5, m6α), 4.19 (dd, 1H, J=5.0, 12.0 Hz, H-6β), 4.98 (s, 2H, PhCH$_2$), 5.28 (t, 1H, J=10.1 Hz, H-m4), 5.37 (m, 1H, H-m2), 5.45 (d, 1H, J=2.2 Hz, H-m1), 5.49 (d, 1H, J=3.4 Hz, H-m3), 7.00 (d, 2H, J=8.4 Hz, H-a2), 7.25 (d, 2H, J=8.4 Hz, H-a3). $^{13}$C NMR (10% CD$_3$OD/CDCl$_3$, 75 MHz) δ 14.0 (SCH$_3$), 20.6 (3 carbons, Ac×3), 20.8 (Ac), 56.3 (C-d5), 62.2 (C-m2), 66.0 (C-m3), 66.4 (PhCH$_2$), 69.0, 69.2, 69.4 (C-m6, m4, m5), 71.2, 71.8, 75.8, 77.4 (C-d4, d3, d1, d2), 95.8 (C-m1), 116.5 (C-a2), 129.8 (C-a3), 131.2 (C-a4), 155.5 (OCONH), 156.5 (C-a1), 170.1 (MeCO), 170.3 (2 carbons, MeCO×2), 171.0 (MeCO). MALDI-TOF MS (m/z) calcd for C$_{28}$H$_{37}$NO$_{15}$SNa: 682.1782; found 682.1110 [M+Na]$^+$.

(1,4/2,3,5)-5-[4-(2,3,4,6-tetra-O-acetyl-α-D-mannopyranosyloxy)-benzyloxycarbonyl]amino-1,2,3,4-cyclopentanetetrol (13). To a suspension of 11 (209 mg, 0.338 mmol) and 6 (hydrochloride salt, 94 mg, 0.506 mmol) in DMF (4 ml) was added Et$_3$N (188 μl, 1.35 mmol). The reaction mixture was stirred for 18 h, after which it was concentrated in vacuo. The residue was purified by flash chromatography over Iatrobeads β-8% MeOH in CH$_2$Cl$_2$) to give 13 (193 mg, 91%) as white solid. $R_f$=0.20 (1:9 MeOH/CH$_2$Cl$_2$). $^1$H NMR (10% CD$_3$OD/CDCl$_3$, 300 MHz) δ 2.01, 2.02, 2.05, 2.19 (4×s, 12H, 4×CH$_3$, Ac), 3.61 (b, 1H, H-d5), 3.78 (b, 2H, H-d1, d4), 3.88 (b, 2H, H-d2, d3), 4.00-4.10 (m, 2H, H-m5, m6α), 4.24 (dd, 1H, J=4.9, 12.1 Hz, H-m6β), 5.00 (s, 2H, PhCH$_2$), 5.34 (t, 1H, J=10.2 Hz, H-m4), 5.42 (b, 1H, H-m2), 5.47-5.54 (m, 2H, H-m1, m3), 6.51 (d, 1H, J=5.6 Hz, NH), 7.04 (d, 2H, J=8.2 Hz, H-a2), 7.28 (d, 2H, J=8.4 Hz, H-a3). $^{13}$C NMR (10% CD$_3$OD/CDCl$_3$, 75 MHz) δ 20.5 (CH$_3$), 20.6 (2 carbons, CH$_3$×$_2$), 20.7 (CH$_3$), 61.8 (C-d5), 62.1 (C-m2), 65.9 (C-m3), 66.5 (PhCH$_2$), 69.0, 69.1, 69.3 (C-m6, m4, m5), 74.6 (C-d2, d3), 79.1 (C-d1, d4), 95.7 (C-m1), 116.5 (C-a2), 129.7 (C-a3), 130.9 (C-a4), 155.4 (OCONH), 158.0 (C-a1), 170.0 (MeCO), 170.2 (2 carbons, MeCO×2), 170.9 (MeCO). MALDI-TOF MS (m/z) calcd for C$_{27}$H$_{35}$NO$_{16}$Na: 652.1854; found 652.2129 [M+Na]$^+$.

1D-(1,2,3,4/5)-4-[4-(α-D-mannopyranosyloxy)-benzyloxycarbonyl]amino-5-(methylsulfanyl)cyclopentane-1,2,3-triol (1). Methanolic ammonia (7 N, 10 ml) was added to a cooled (0° C.) solution of compound 12 (32 mg, 0.0517 mmol) in MeOH (2 ml). The reaction mixture was stirred at 0° C. for 5 h, after which the solvents were concentrated in vacuo. The residue was purified over P2 size exclusion chromatography (1% n-butanol in water) to give 1 (24 mg, 94%) as white solid. $^1$H NMR (D$_2$O, 300 MHz) δ 1.99 (s, 3H, SCH$_3$), 2.84 (t, 1H, J=8.1 Hz, H-d5), 3.56-3.69 (m, 4H, H-m4, m5, m6), 3.72-3.84 (m, 2H, H-d4, d1), 3.89-4.00 (m, 3H, H-d2, d3, m3), 4.05 (dd, 1H, J=1.9, 3.1 Hz, H-m2), 4.96 (s, 2H, PhCH$_2$), 5.50 (d, 1H, J=1.5 Hz, H-m1), 7.05 (d, 2H, J=8.5 Hz, H-a2), 7.28 (d, 2H, J=8.5 Hz, H-a3). $^{13}$C NMR (D$_2$O, 75 MHz) δ 12.6 (SCH$_3$), 54.8, 56.1, 60.8, 66.8, 66.9, 70.0, 70.6, 70.8, 71.5, 73.5, 74.0, 98.3 (C-m1), 117.3 (C-a2), 129.8 (C-a3), 131.0 (C-a4), 155.5 (OCONH), 158.2 (C-a1). MALDI-TOF MS (m/z) calcd for C$_{20}$H$_{29}$NO$_{11}$SNa: 514.1359; found 514.1320 [M+Na]$^+$.

(1,4/2,3,5)-5-[4-(α-D-mannopyranosyloxy)-benzyloxycarbonyl]amino-1,2,3,4-cyclopentanetetrol (2). Hydrazine monohydrate (5 ml) was added to a colded (0° C.) solution of 13 (138 mg, 0.219 mmol) in MeOH (20 ml). After stirring the reaction mixture at 0° C. for 5 h, it was quenched by addition of acetone and the mixture was concentrated in vacuo. The residue was purified over P2 size exclusion chromatography (1% n-butanol in water) to give 2 (101 mg, 99%) as white solid. $^1$H NMR (D$_2$O, 300 MHz) δ 3.44 (t, 1H, J=8.1 Hz, H-d5), 3.50-3.67 (m, 6H, H-m4, m5, m6, d2, d3), 3.77 (b, 2H, H-d1, d4), 3.89 (dd, 1 H, J=3.4, 9.1 Hz, H-m3), 3.99 (b, 1H, H-m2), 4.89 (s, 2H, PhCH$_2$), 5.43 (b, 1H, H-m1), 6.97 (d, 2H, J=8.4 Hz, H-a2), 7.21 (d, 2H, J=8.4 Hz, H-a3). $^{13}$C NMR (D$_2$O, 75 MHz) δ 60.3 (C-d5), 60.8, 66.7 (2 carbons), 70.1, 70.6, 73.5, 73.7, 78.2 (C-d2, d3), 98.2 (C-m1), 117.2 (C-a2), 129.8 (C-a3), 130.8 (C-a4), 155.5 (OCONH), 158.5 (C-a1). MALDI-TOF MS (m/z) calcd for C$_{19}$H$_{27}$NO$_{12}$Na: 484.1431; found 484.2137 [M+Na]$^+$.

1D-(1,2,3,4/5)-4-[4-(2,3,4,6-tetra-O-acetyl-α-D-mannopyranosyloxy)-benzyloxycarbonyl]amino-1,2,3-tri-O-acetyl-5-(methylsulfanyl)cyclopentane-1,2,3-triol (14). Compound 1 (8 mg, 0.0163 mmol) was dissolved in pyridine (2 ml) and acetyl anhydride (0.5 ml). The reaction mixture was stirred for 5 h, after which the solvents were evaporated in vacuo. The residue was purified by flash chromatography over silica (1:1 to 1:0 EtOAc/hexanes) to give 14 (10 mg, 78%) as white solid. R$_f$=0.15 (1:1 hexanes/EtOAc). $^1$H NMR (CDCl$_3$, 300 MHz) δ 1.99-2.01 (m, 24H, 7×CH$_3$ Ac, SCH$_3$), 3.10 (t, 1H, J=7.2 Hz, H-d5), 4.07 (m, 2H, H-m5, m6α), 4.28 (m, 2H, H-m6β, d4), 5.07 (s, 2H, PhCH$_2$), 5.14 (t, 1H, J=6.3 Hz, H-d1), 5.27-5.34 (m, 2H, H-d2, d3), 5.36-5.44 (m, 2H, H-m4, m2), 5.52 (d, 1H, J=1.5 Hz, H-m1), 5.57 (dd, 1 H, J=3.6, 10.0 Hz, H-m3), 7.09 (d, 2H, J=8.6 Hz, H-a2), 7.32 (d, 2H, J=8.6 Hz, H-a3). MALDI-TOF MS (m/z) calcd for C$_{34}$H$_{43}$NO$_{18}$SNa: 808.2099; found 808.2131 [M+Na]$^+$.

(1,4/2,3,5)-5-[4-(2,3,4,6-tetra-O-acetyl-α-D-mannopyranosyloxy)-benzyloxycarbonyl]amino-1,2,3,4-tetra-O-acetyl-1,2,3,4-cyclopentanetetrol (15). Compound 2 (22.6 mg, 0.0490 mmol) was dissolved in pyridine (2 ml) and acetyl anhydride (0.5 ml). The reaction mixture was stirred for 5 h, after which the solvents were evaporated in vacuo. The residue was purified by flash chromatography over silica (1:1 to 1:0 EtOAc/hexanes) to give 15 (39.1 mg, 92%) as white solid. R$_f$=0.50 (1:2 hexanes/EtOAc). $^1$H NMR (CDCl$_3$, 300 MHz) δ 2.01-2.01 (m, 21H, 7×CH$_3$, Ac), 2.19 (s, 3H, CH$_3$, Ac), 4.01-4.09 (m, 2H, H-d5, m5), 4.11 (dd, 1H, J=7.2, 14.3 Hz, H-6α), 4.27 (dd, 1H, J=5.3, 12.1 Hz, H-m6β), 5.02 (s, 2H, PhCH$_2$), 5.17 (dd, 2H, J=4.3, 6.0 Hz, H-d1, d4), 5.25 (d, 2H, J=4.1 Hz, H-d2, d3), 5.36 (t, 1H, J=10.1 Hz, H-m4), 5.43 (dd, 1 H, J=1.7, 3.4 Hz, H-m2), 5.51 (d, 1H, J=1.5 Hz, H-m1), 5.54 (dd, 1H, J=3.5, 10.1 Hz, H-m3), 7.06 (d, 2H, J=8.6 Hz, H-a2), 7.28 (d, 2H, J=8.6 Hz, H-a3). MALDI-TOF MS (m/z) calcd for C$_{35}$H$_{43}$NO$_{20}$Na: 820.2276; found 820.2220 [M+Na]$^+$.

Stability measurements. A solution of compound 1 or 2 (0.4 mM) in deuterated sodium acetate buffer (100 mM; pH 4.0; 0.2 ml) in a NMR tube was incubated at 37° C. for 6 days. $^1$H NMR spectra were recorded every day. No decomposition of product was observed.

Kinetic measurements. A solution of compound 1 or 2 (0.08 µmol) and human lysosomal mannosidase (HLM, 0.02 Unit) in deuterated sodium acetate buffer (0.1 M; pH 5.6; 0.2 ml) was incubated at 37° C., and $^1$H NMR spectra (600 MHz) were recorded at different time intervals. Relevant signals were integrated to determine the rate of enzymatic hydrolysis, and the appearance of the intermediate and the final product.

Self-decomposition half-time measurements. A solution of compound 2 (0.08 µmol) and Jack Bean mannosidase (JBM) (1.4 Units) in deuterated 0.2 M phosphate/0.1 M citrate buffer (pH=4.0, 4.5, 5.0, 5.5, 6.0 or 6.5; 0.2 ml) was incubated at 37° C. or 25° C., and $^1$H NMR spectra (600 MHz) were recorded at different time intervals. Relevant signals were integrated to determine the appearance of the intermediate 4 and the final product 6, and the decomposition rate.

Negative enzyme control experiments. A solution of compound 1 or 2 (0.004 mmol) and α-glucosidase, α-galactosidase or α-L-fucosidase (0.1 Unit) in MES buffer (0.05 M; pH 6.8 for α-glucosidase, pH 6.5 for α-galactosidase or pH 5.5 for α-L-fucosidase; 1 ml) was incubated at 37° C. for 20 h, after which the reaction mixture was freezing-dried, and the solid residue was analyzed by $^1$H NMR spectrometry and mass spectrometry. No decomposition of product was observed.

Cell maintenance. MDAY-D2 lymphoma cells, provided by Dr. K. Moremen (CCRC, UGA, Athens, Ga.), were cultured in Eagle's Minimum Essential Medium (MEM) with 2 mM L-glutamine, Earle's Balanced Salt Solution, 1.5 g/L sodium bicarbonate, 0.1 mM non-essential amino acids, and 1.0 mM sodium pyruvate (ATCC) supplemented with penicillin (100 I.U./mL)/streptomycin (100 µg/mL; Mediatech) and heat-inactivated fetal bovine serum (h-iFBS; 10%; Hyclone). The cells were maintained in a humid 5% CO$_2$ atmosphere at 37° C. New batches of frozen cell stock were grown up every 2 months and growth morphology was evaluated.

Inhibition of cell surface polylactosamine biosynthesis. MDAY-D2 cells were plated at 5×10$^4$ cells/well into 6-well cell culture plates (Costar) in the absence (control) or presence of compounds 14 or 15 (0.1-100 µM) and incubated for 48 h in culture medium containing 2% h-iFBS. On average 1×10$^6$ cells per well were obtained after incubation for 48 h. Cells were harvested by centrifugation (1,400 rpm for 5 min) and lysed in lysis buffer (10 mM Tris, pH 7.5, 0.15 M NaCl, 0.5% Triton X-100, 2 mM phenylmethylsulfonyl fluoride, 1% aprotinin) on ice. After centrifugation (14,000 rpm for 10 min at 4° C.), the supernatants were stored at −80° C. Protein concentrations were determined using the BCA reagent (Pierce) and cellular proteins (10 µg) were separated by SDS-PAGE using 4-20% linear gradient polyacrylamide gels (Bio-Rad). Separated proteins were electrotransferred onto nitrocellulose membranes (Hybond-P; Amersham). The blots were incubated with 5 µg/mL fluorescein labeled *Phaseolus vulgaris* Leucoagglutinin (PHA-L; Vector Laboratories) in PBS/0.1% BSA for 1 h at room temperature. Fluorescence bands were imaged at 495 nm (absorbance)/520 nm (emission) and the intensity scanned by laser beam densitometry (Typhoon 9410 Imager; Amersham Biosciences).

Example II

Design and Synthesis of Selective Glycosidase Inhibitors

Cells that have undergone oncogenic transformation often display abnormal cell surface oligosaccharides. These changes in glycosylation are important determinants of the stage, direction and fate of tumor progression. Inhibition of the mannose trimming enzyme human Golgi α-mannosidase II (HGMII), which acts late in the N-glycan processing pathway, provides one route to blocking the oncogene-induced changes in cell surface oligosaccharide structures.

Figure 5:
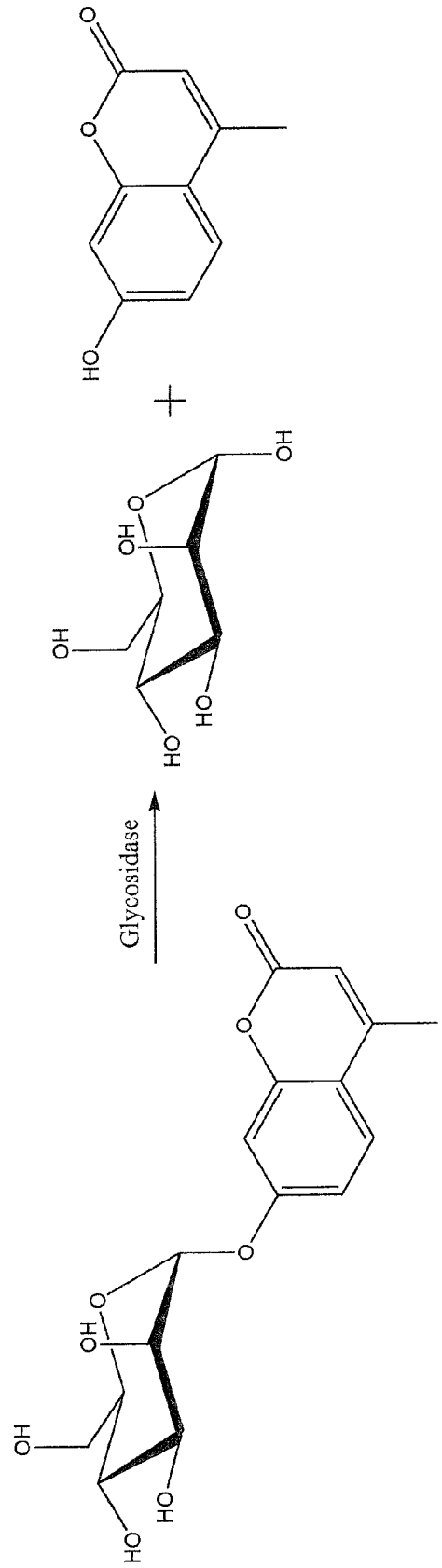
FIG. 5 shows the selectivity of the glycosidase inhibitor swainsonine.

A serious side effect of most mannosidase inhibitors is, however, the blockage in oligosaccharide catabolism arising from inhibition of a related catabolic α-mannosidase found in lysosomes. The development of a drug appropriate for antimetastatic therapy requires a compound which specifically inhibits Golgi α-mannosidase II without affecting the function of lysosomal mannosidase (HLM). Many of the known glycosidase inhibitors exhibit low selectivity. For example, FIG. 5 shows the selectivity of the glycosidase inhibitor swainsonine. Our goal is to increase the selectivity of mannosidase inhibitors using rational drug design.

We synthesized an inhibitor, N-benzyl mannostatin, which we expected to be more selective for HGMH than mannostatin A. It was expected that the benzyl moiety would interact with the aromatic residues of the analogous *drosophila* Golgi α-mannosidase II (dGMII) binding site, thereby increasing its affinity. However, it was found that this compound had, in fact, slightly reduced affinity, indicating that the benzyl group cannot make favorable interactions with the enzyme. The finding was ultimately explained by careful examination of the crystal structure of dGMII with the synthetic inhibitor; see Kawatkar et al., J. Am. Chem. Soc., 128, 8310-8319 (2006).

Figure 6:
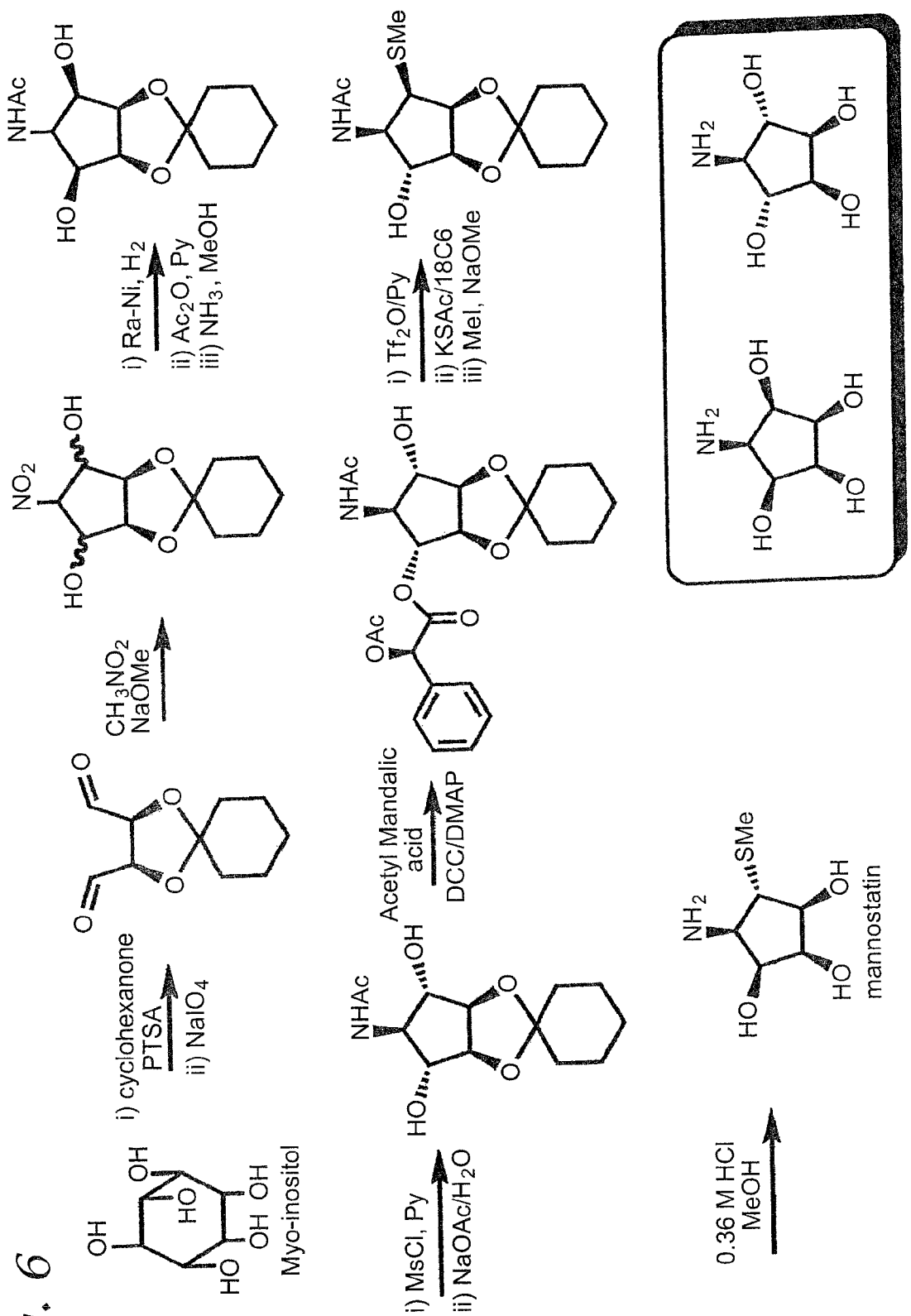
FIG. 6 shows a chemical synthesis of mannostatin A.
Figure 7:
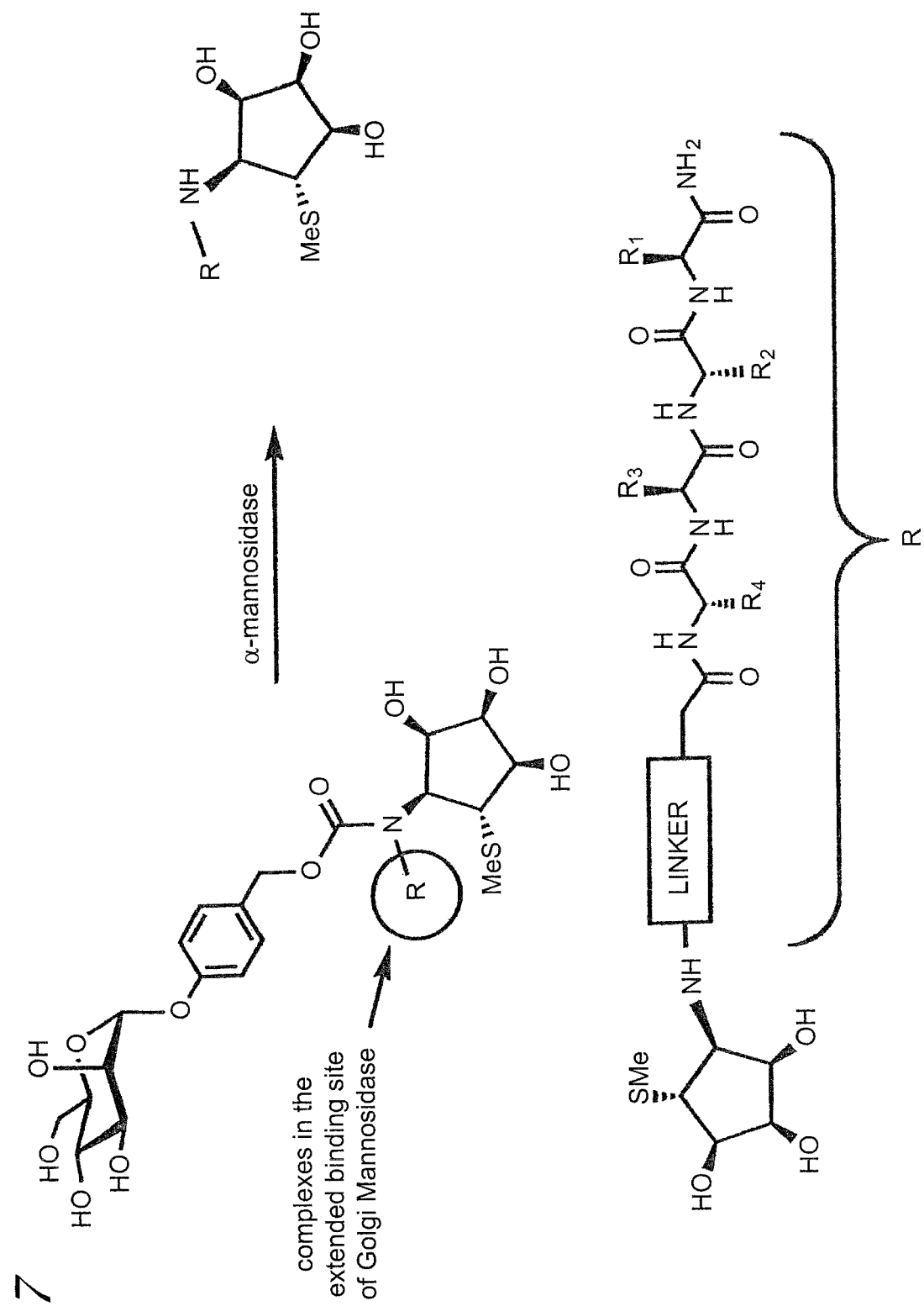
FIG. 7 shows an illustrative modified mannostatin. A inhibitor.
Figure 8:
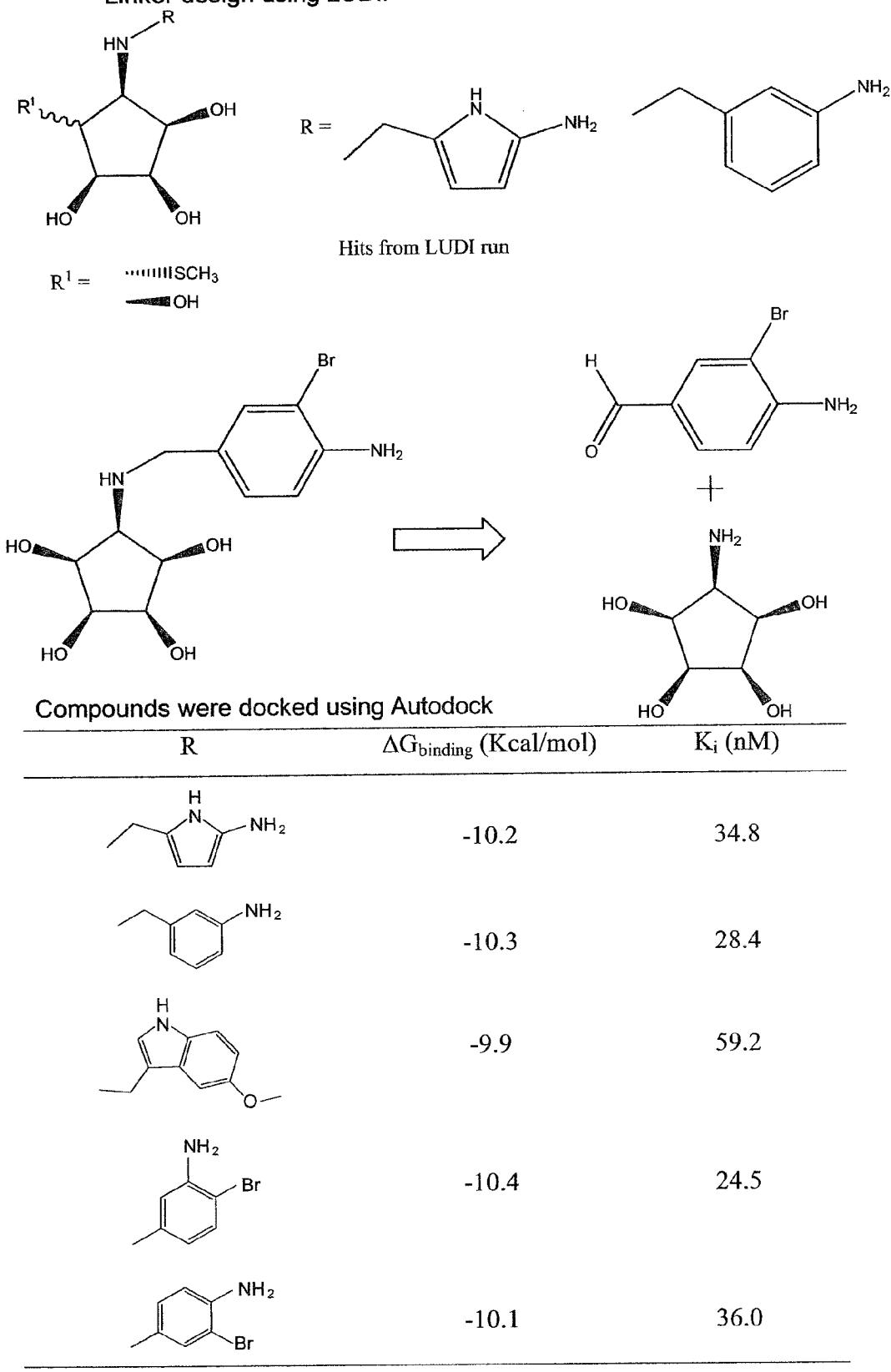
FIG. 8 shows additional illustrative mannostatin A inhibitors.
Figure 9:
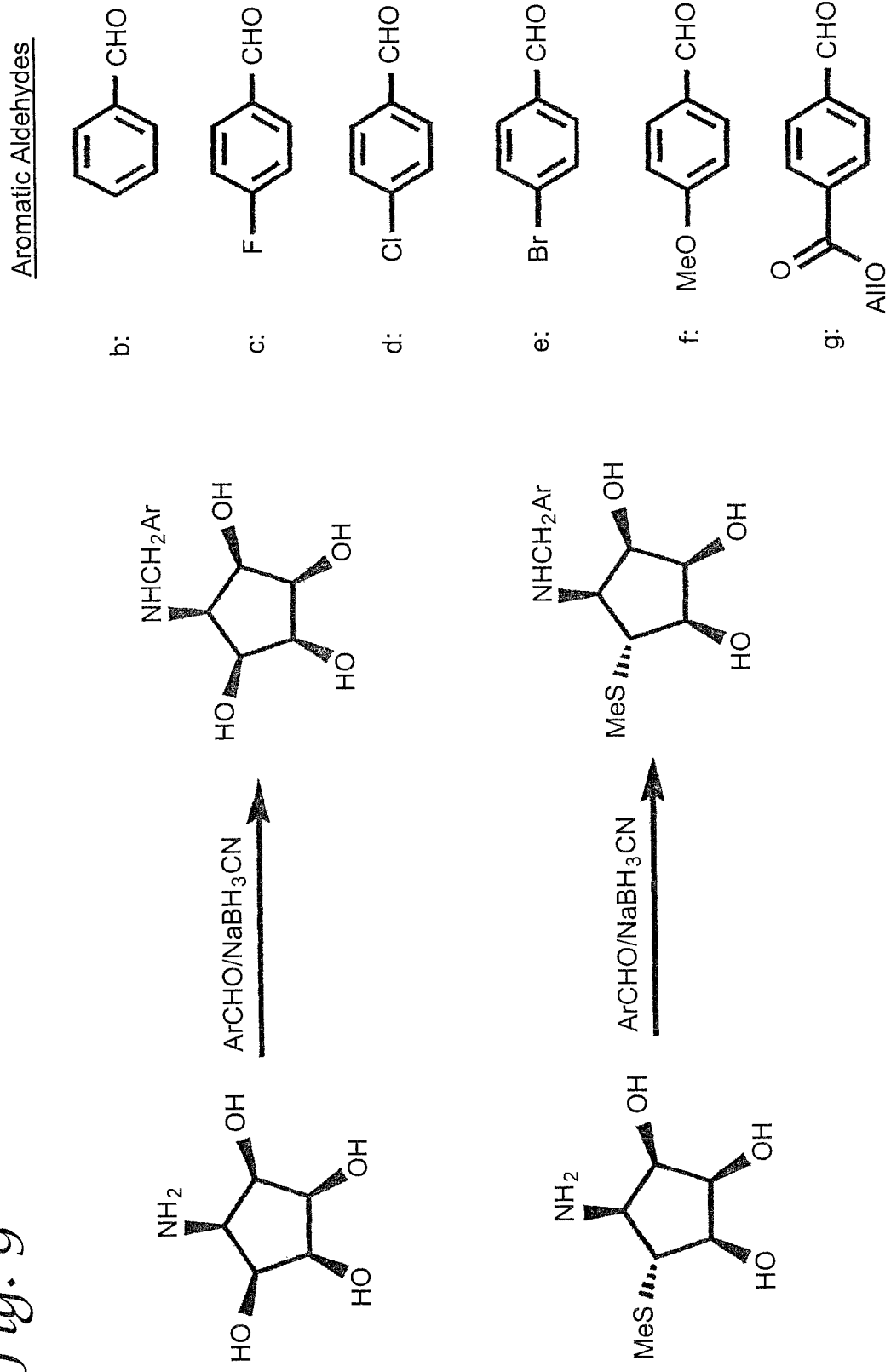
FIG. 9 shows a procedure for chemically modifying mannostatin A and a control compound using reductive amination.

FIG. 6 shows a chemical synthesis of mannostatin A. Derivatives in which the primary amine, —NH$_2$, is replaced by a secondary amine, —NHR, with R being an aliphatic or aromatic group, are also contemplated for use in the invention. See, e.g., FIG. 7, showing a mannostatin A derivatized with a peptide sequence. Other inhibitor compounds based on the mannostatin structure but containing linkers designed using LUDI (Insight II, Accelrys) are shown in FIG. 8. Derivatization of mannostatin A using reductive amination with various aromatic aldehydes is shown in FIG. 9.

Inhibition of human Golgi mannosidase II (HGMII) and human lysosomal mannosidase (HLM) by selected derivatized mannostatins and their analogous controls is shown in FIG. 10.

It is expected that combinatorial drug design will yield modified inhibitors with improved properties, such as better binding to the extended binding site of Golgi mannosidase. Combinatorial techniques that can be used to modify an inhibitor such as mannostatin A include parallel combinatorial modification by peptides and "mix and split" combinatorial modification by peptides in combination with screening by frontal affinity chromatography with MS-detection (FIG. 11).

ADDITIONAL REFERENCES

Varki, Glycobiology 1993, 3, 97.
Dwek, Chem. Rev. 1996, 96, 683.
Kolter et al., Angew. Chem., Int. Ed. 1999, 38, 1532.
Dennis et al., Bioessays 1999, 21, 412.
Fuster et al., Nature Reviews Cancer 2005, 5, 526.
Dube et al., Nature Reviews Drug Discovery 2005, 4, 477.
Dennis et al., Biochim. Biophys. Acta 1999, 1473, 21.
Goss et al., Clin. Cancer Res. 1995, 1, 935.
Lillelund et al., Chem. Rev. 2002, 102, 515.
Berecibar et al., Chem. Rev. 1999, 99, 779.
Asano et al., Tetrahedron: Asymmetry 2000, 11, 1645.
Heightman et al., Angew. Chem., Int. Ed. 1999, 38, 750.
von Itzstein et al., Curr. Med. Chem. 1997, 4, 185.
Pardee et al., Gene 2003, 321, 17.
King et al., J. Am. Chem. Soc. 1994, 116, 562.
de Groot et al., J. Org. Chem. 2001, 66, 8815.
Ogawa et al., Bioorg. Med. Chem. Lett. 2000, 10, 1047.
Wilson et al., Org. Lett. 1999, 1, 443.
Li et al., Chem. Bio. Chem. 2004, 5, 1220.
Elbein, FASEB J. 1991, 5, 3055.
Sarkar et al., Proc. Natl. Acad. Sci. USA 1995, 92, 3323.
Dennis et al., Cancer Res. 1990, 50, 1867.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A conjugated compound comprising:
   a first constituent comprising an enzymatic substrate comprising a mannoside; and
   a second constituent covalently linked to the first constituent, the second constituent comprising a mannosidase inhibitor selected from the group consisting of mannostatin A, mannostatin B, or a mannostatin A derivative wherein the methyl thioether group (—S—CH$_3$) group of mannostatin A is replaced by a phenyl thioether group (—S—Ph), a methoxy group (—O—CH$_3$) or a phenoxy group (—O—Ph); and
   wherein the covalent linkage between the first and second constituents can be enzymatically cleaved by a mannosidase to release the mannosidase inhibitor; and wherein the mannosidase inhibitor, when released from the conjugated compound, inhibits the activity of the mannosidase.

2. The conjugated compound of claim 1 wherein the second constituent further comprises a linking group, such that the first constituent is covalently linked to the linking group, which in turn is covalently linked to the mannosidase inhibitor.

3. The conjugated compound of claim 1 wherein enzymatic cleavage of the covalent linkage between the first constituent and the second constituent releases the second constituent, which then self-fragments to yield the mannosidase inhibitor.

4. The conjugated compound of claim 1 wherein the first or second constituent further comprises a moiety that increases metabolic stability or facilitates cellular uptake.

5. The conjugated compound of claim 4 wherein the first or second constituent is acetylated.

6. The conjugated compound of claim 2 wherein the linking group is an O-linked group selected from the group consisting of 4-hydroxyl benzyl carbamate, a "trimethyl lock", coumarin, 2-hydroxyphenyl carbamate, and 2-hydroxypropyl carbamate.

7. The conjugated compound of claim 2 wherein the linking group is an N-linked group selected from the group consisting of 4-aminobenzyl carbamate, 2-aminophenyl carbamate, and N,N'-dimethylethylenediamine carbamate.

8. The conjugated compound of claim 2 wherein the mannosidase inhibitor is mannostatin A, and wherein linking group is attached to the amine group of mannostatin A.

* * * * *